United States Patent
Belkind et al.

(10) Patent No.: US 8,278,480 B2
(45) Date of Patent: Oct. 2, 2012

(54) SALTS, AQUEOUS LIQUID COMPOSITIONS CONTAINING SALTS OF S-(+)-ABSCISIC ACID AND METHODS OF THEIR PREPARATION

(75) Inventors: Benjamin A. Belkind, Wilmette, IL (US); Daniel F. Heiman, Libertyville, IL (US); Zhengyu Huang, Buffalo Grove, IL (US); Xiaozhong Liu, Vernon Hills, IL (US); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 509 days.

(21) Appl. No.: 12/508,108

(22) Filed: Jul. 23, 2009

(65) Prior Publication Data

US 2010/0152046 A1 Jun. 17, 2010

Related U.S. Application Data

(60) Provisional application No. 61/083,202, filed on Jul. 24, 2008.

(51) Int. Cl.
*C07C 59/46* (2006.01)

(52) U.S. Cl. .................................................. 562/508

(58) Field of Classification Search ................ None
See application file for complete search history.

(56) References Cited

U.S. PATENT DOCUMENTS

| 4,209,530 A | 6/1980 | Visscher |
| 4,434,180 A | 2/1984 | Visscher |
| 6,586,617 B1 | 7/2003 | Tabuchi et al. |
| 2006/0084573 A1 | 4/2006 | Grech et al. |
| 2006/0292215 A1 | 12/2006 | Romero |

FOREIGN PATENT DOCUMENTS

GB 1251867 11/1971

OTHER PUBLICATIONS

Southwick et al. Plant Physiology, 1986, 81, 323-325.*
Mauseth, "Botany an introduction to plant biology", 1991 Philadelphia Saundera pp. 348-415.
Raven et al., Biology of plants fifth edition, 1992 New York Worth. pp. 545-572.
Milborrow, "The chemistry and physiology of abscisic acid", Am. Rev. Plant Physiol. 1974, 25 pp. 259-307.
Zeevart et al., "Metabolism and physiology of abscsic acid", 1988 Ann. Rev. Plant Physiol. Plant Mot. Biol. 39, pp. 439-473.
Kriedemann et al., "Abscisic acid and stomatal regulation", 1972, Plant Physiol. 49, pp. 842-847.
Zhang et al., "Purification and identification of a 42-kilodalton abscisic acid-specific-binding protein from epidermis of broad bean leaves", Feb. 2002, Plant Physiology, vol. 128, pp. 714-725.
Railton et al., "Effects of abscisic acid on the levels of endogenous gibberellins-like substances in Solanum andigena", 1973 Planta (Berl.) 112, pp. 65-69.
Bonnafous et al., "Nouvelle methode de resolution optique de l 'acide abscisique", 1973 Tetrahedron Letters No. 13, pp. 1119-1122.
Blumenfeld et al., "Cuticular penetration of abscisic acid", May 5, 1972, Planta (Berl.) 107, pp. 261-268.
Finkelstein et al., "Abscisic Acid Biosynthesis and Response", 2002 The Arabidopsis Book, American Society of Plant Biologists, pp. 1-52.

* cited by examiner

*Primary Examiner* — Yevegeny Valenrod
(74) *Attorney, Agent, or Firm* — Wood, Philips, Katz, Clark & Mortimer

(57) ABSTRACT

The present invention generally relates to salts of S-(+)-abscisic acid having enhanced performance, aqueous liquid compositions containing these enhanced performance salts of S-(+)-abscisic acid and methods of their preparation for agricultural use.

25 Claims, No Drawings

SALTS, AQUEOUS LIQUID COMPOSITIONS CONTAINING SALTS OF S-(+)-ABSCISIC ACID AND METHODS OF THEIR PREPARATION

FIELD OF THE INVENTION

The present invention generally relates to salts of (S)-(+)-abscisic acid having enhanced performance, aqueous liquid compositions comprising such salts of (S)-(+)-abscisic acid and methods of their preparation for agricultural use.

BACKGROUND OF THE INVENTION

Abscisic acid is a naturally occurring plant hormone which acts primarily to inhibit growth of plants, maintain dormancy of buds, inhibit fruit-ripening, activate the pathogen resistance response defense, induce senescence in already-damaged cells and their proximate neighbors, and help the plant tolerate stressful conditions, particularly the lack of sufficient water. See Arteca, R. (1996), Plant Growth Substances: Principles and Applications. New York: Chapman & Hall; Mauseth, J. D. (1991), *Botany: An Introduction to Plant Biology*. Philadelphia: Saunders. pp. 348-415; Raven, P. H., Evert, R. F., and Eichhorn, S. E. (1992), *Biology of Plants*. New York: Worth. pp. 545-572.

Abscisic acid owes its name to the belief that this plant growth regulator causes the abscission of leaves from deciduous trees in the fall. Absicin II and dormin are names previously used for this plant hormone. The chemistry and physiology of abscisic acid and its analogs is described by Milborrow, Ann Rev. Plant Physiol. 1974, 25, 259-307.

The naturally occurring enantiomeric form of abscisic acid is (s)-(+)-abscisic acid. In some literature reports the other enantiomer, (R)-(−)-abscisic acid is seen to be biologically inactive. In other research, it has been reported that (R)-(−)-abscisic acid also has some biological activities, however, they are often different from those of the (s)-(+)-enantiomer. See, Zeevart J. A. D. and Creelman, R. A. (1988) *Metabolism and Physiology of Abscisic Acid*, Annu. Rev. Plant Physiol. Plant Mol. Biol. 39, 439-473. Thus for use in a commercial agricultural product, the compositions of the present invention, comprising specific salts of and salt combinations with (S)-(+)-abscisic acid as the active ingredient are preferable to the prior art compositions comprising various racemic or pure enantiomeric forms of abscisic acid or their common salts, such as the sodium, potassium or ammonium salts, since substantially enhanced bioactivity is obtained without the risk of the phytotoxicity on the target plants as is often found when employing surfactants to enhance biological efficacy.

The stereochemistry of the side chain of the major part of naturally occurring abscisic acid is 2-cis-,4-trans-, since that is the isomer that is produced biosynthetically by all green plants and some microorganisms. A smaller amount of the (S)-(+)-2-trans-,4-trans-isomer is also found to occur naturally, since it is produced photolytically by the action of sunlight on the (S)-(+)-2-cis-,4-trans-isomer. The (S)-(+)-2-trans-,4-trans-isomer is reported to be biologically inactive. See P. E. Kreidelmann, et al., Plant Physiol. 49, 842-847 (1972), D.-P. Zhang, et al., Plant Physiol. 128, 714-725, (2002) or X.-C. Yu, et al., Plant Physiol. 140, 558-579 (2006).

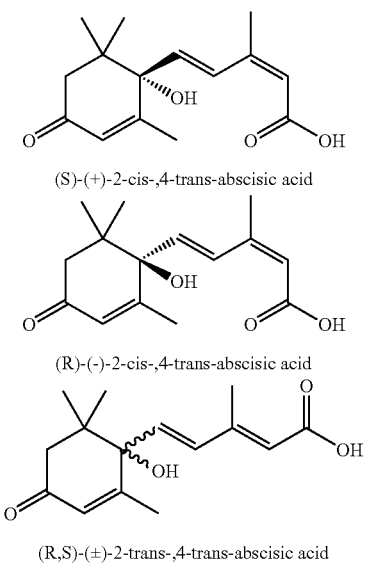

(S)-(+)-2-cis-,4-trans-abscisic acid (R)-(−)-2-cis-,4-trans-abscisic acid (R,S)-(±)-2-trans-,4-trans-abscisic acid Prior art (U.K. Pat. No. 1251867 and Railton and Wareing, Planta 112, 65-69, 1973) teaches, inter alia, preparation of amine salts of racemic abscisic acid. A salt of racemic (R,S)-(±)-2-trans-,4-trans-abscisic acid with the chiral alkaloid brucine was prepared as a means of resolving a small quantity of the racemate in order to study the physical properties of its enantiomers (J. C. Bonnafous, et al., Tetrahedron Letters, 1119-1122, 1973). Pending U.S. patent application Ser. No. 12/011,845 filed Jan. 30, 2008, discloses certain salts of (S)-(+)-abscisic acid, including the ammonium, sodium, potassium, lithium, magnesium, calcium metal salts as well as salts formed with simple primary, secondary and tertiary organic amines. However, this patent application does not disclose salts of (S)-(+)-cis-,trans-abscisic acid with heavy alkali metals, quaternary ammonium cations or guanidines, nor does it disclose combinations of common salts of (S)-(+)-abscisic acid with iodide salts of alkali metals, quaternary ammonium cations or guanidines as performance-enhancing additives.

As noted above, abscisic acid is a carboxylic acid, and thus in a medium having an acidic pH, it is protonated and in its neutral undissociated form. This uncharged, undissociated form is more lipophilic than a salt of abscisic acid, and penetration of the uncharged acid form into the plant cuticle would be favored relative to the charged, dissociated form of abscisic acid present at higher pH (Blumenfeld and Bukovac 1972, Planta 107: 261-268). The uncharged, undissociated form of abscisic acid would be expected to cross cell membranes from the apoplast into the cytosol more easily than a salt form. In spite of this, we have surprisingly found that treatments comprising the specific salts of abscisic acid of the present invention have much better biological activity when compared with similar treatments comprising the acid form of (S)-(+)-abscisic acid at the same concentration and also much better than the salts of (S)-(+)-abscisic acid with common counterions such as sodium, potassium or ammonium.

Abscisic acid was first defined in the early 1960s as a growth inhibitor accumulating in abscising cotton fruit and in leaves of sycamore trees photoperiodically induced to become dormant. See, Finkelstein R R, Rock C D (2002), *Abscisic Acid Biosynthesis and Response*, The Arabidopsis Book Vol. 45, No. 1 pp. 1-48. Since then, abscisic acid has been shown to regulate many aspects of plant growth and development, including embryo maturation, seed dormancy, germination, cell division and elongation, etc. Although abscisic acid has historically been thought of as a growth inhibitor, young tissues have high abscisic acid levels, and abscisic acid-deficient mutant plants are severely stunted because their ability to reduce transpiration and establish turgor is impaired. Exogenous abscisic acid treatment of mutants restores normal cell expansion and growth.

Abscisic acid is thought to initiate its effects on cells through binding to receptor proteins, although their identities and locations are still largely unknown. Activation of the putative receptor(s) causes a chain of events that results in rapid changes in ion channels and slower changes in the pattern of gene transcription. While many individual components of this chain of events have been identified, a complete picture has not yet been obtained.

Commercial formulations comprising abscisic acid are used in agriculture for various purposes, such as improving stress tolerance of plants, slowing their growth rate, adjusting flowering phase, and other purposes. Abscisic acid has also been reported to possess insect inhibition qualities. See U.S. Pat. Nos. 4,434,180 and 4,209,530 to Visscher. Abscisic acid in a powdered form is currently commercially available from Lomon Biotechnology Company, Ltd., a Chinese company, which markets it as a substance that, among other uses, improves the yield and quality of certain crops.

However, one of the problems associated with prior art abscisic acid formulations is abscisic acid's relatively poor solubility in water: not more than about 3 grams per liter or alternatively, less than 0.3% by weight will dissolve at ordinary temperatures. A concentration of about 3000 parts per million (ppm) is the highest concentration that can be achieved in pure water at room temperature. Abscisic acid solubility in hard water is even less. While abscisic acid has better solubility in some organic solvents, liquid formulations of abscisic acid in organic solvents are unacceptable in some contexts because of flammability, toxicity or pollution considerations. For example, the Environmental Protection Agency of the U.S. state of California is currently requiring that liquid formulations of agricultural products contain no volatile organic solvent, and several other U.S. states are considering similar regulations. Nonvolatile organic solvents have the detriment that, since they do not evaporate, they remain in the agricultural product as it impinges upon and is absorbed into the target plant, with a probability of causing phytotoxicity and contaminating food products, since the amount of the solvent greatly exceeds the amount of active ingredient applied. Moreover, even in many organic solvents, the solubility of abscisic acid is too low to be of practical value. For example, abscisic acid is poorly soluble in propylene glycol, a relatively desirable solvent for agricultural formulations because of its low toxicity and high flash point.

A further problem observed with concentrated solutions of (S)-(+)-abscisic acid in organic solvents is that it is difficult to prepare more dilute solutions by dilution into water without having a portion of the (S)-(+)-abscisic acid precipitate out in a gummy form that redissolves only very slowly and with great difficulty. This is of practical importance because a major use of (S)-(+)-abscisic acid in agriculture or horticulture is for the reduction of transpiration in nursery plants being prepared for transplantation or for sale to consumers, for which purpose (S)-(+)-abscisic acid is often applied by means of an injection system and automatic or hand applicators. The solution for use in such an applicator must be a concentrate between about 50 and 100 times more concentrated than the dose rate that actually reaches the plants when they are treated by foliar spray or drench. Thus for a typical application to nursery plants of 60 to 600 ppm, the concentrate must contain between 3000 and 60,000 ppm of (S)-(+)-abscisic acid in a solution that will mix instantly and completely with the water flowing through the hose, in such a way that there is no possibility of formation of a precipitate that would clog the nozzle through which the water containing active ingredient is applied to the plants or the growing media of the plants. As explained above, the solubility of (S)-(+)-abscisic acid in water is not greater than 3000 ppm at ordinary ambient temperature, so such an intermediate solution cannot practically be prepared in water. A solution of (S)-(+)-abscisic acid in an organic solvent cannot be used in such an injection applicator, because precipitation of the active ingredient will occur during the mixing into the water flowing in the system, and the spray nozzle will be clogged. Because of the solubility limitation, it is also not possible to provide a liquid formulation of the (S)-(+)-abscisic acid in organic solvent at a higher concentration (e.g. 10%) and then at the time of application to prepare an intermediate dilution in water to achieve the desired concentration of 3,000 to 60,000 ppm in the reservoir of the injection applicator.

An identical problem arises in the case of application of (S)-(+)-abscisic acid to a vineyard, orchard or agricultural field through an irrigation system, a practice commonly known as chemigation. Again, such a system requires a concentrated solution of the active ingredient in a liquid solvent in such a form that the solution is instantly and completely miscible with a stream of water flowing through the irrigation system. If any precipitation were to occur, it would block the nozzles (known as emitters) through which the water and dissolved active ingredient reach the target plants. Again in this situation a formulation consisting of an organic solution of (S)-(+)-abscisic acid would not be acceptable because of the problem of low water solubility.

While powdered formulations of abscisic acid are available, it is often more convenient to use concentrated liquid solutions instead of powders. Therefore, there is an unmet need in the art for abscisic acid formulations comprising salts of (S)-(+)-abscisic acid which are much more soluble in water than the acid itself.

Abscisic acid is expensive. It is currently manufactured in commercial quantities only by fermentation, whereby it is produced in dilute solution mixed with nutrients and biological debris, so extraction and purification is laborious. When (S)-(+)-abscisic acid is applied to plants, uptake is poor, so a large excess must be employed. It is possible to improve uptake of (S)-(+)-abscisic acid by combining it with various surfactants; however, it is well known that the use of surfactants can damage the foliage, flowers and fruits of sensitive plants, producing phytotoxicity and reducing the value or destroying the crop. Therefore an unmet need exists in the art for formulations comprising (S)-(+)-abscisic acid that enhance its biological activity without the possibility of causing damage to the plants to which they are applied.

SUMMARY OF THE INVENTION

The present invention is directed to salts of (S)-(+)-abscisic acid prepared with alkali metal cations of high molecular weight or large steric bulk and to compositions of (S)-(+)-abscisic acid comprising certain additional components that enhance its biological activity.

In a further embodiment, the present invention is generally directed to aqueous compositions comprising an effective amount of a salt or combination of salts of (S)-(+)-abscisic acid prepared with alkali metal cations of high molecular weight or large steric bulk wherein the concentration of the (S)-(+)-abscisic acid is at least 0.5% by weight of the aqueous composition. Applicants have unexpectedly discovered that salts of (S)-(+)-abscisic acid prepared with alkali metal cations of high molecular weight or large steric bulk allow for dramatic increases in the biological performance of (S)-(+)-abscisic acid while at the same time increasing the solubility of (S)-(+)-abscisic acid in water so that concentrated solutions can be obtained. As a result, solutions can be obtained with (S)-(+)-abscisic acid concentrations as high as 50% by weight. The present invention allows for the creation of concentrated formulations of (S)-(+)-abscisic acid that are convenient for packaging, storage, transport and handling, but must be diluted prior to use and specifically allows any arbitrary intermediate dilution of these formulations to be made into water without the risk of precipitation of the active ingredient.

Compositions of the present invention generally comprise the salt, an antimicrobial and optionally a non-phytotoxic amount of a surfactant. Other components which enhance the long-term storage stability or the biological activity of the (S)-(+)-abscisic acid may optionally be included.

Representative suitable salts of the invention include, but are not limited to, rubidium or cesium salts, organic quaternary ammonium salts, guanidinium salts or mixtures comprising any number of these. In one embodiment, the organic quaternary ammonium salt is the tetramethylammonium salt. In another embodiment, the organic quaternary ammonium salt is the tetrabutylammonium salt. In another embodiment, the organic quaternary ammonium salt is the choline salt. In yet another embodiment, the guanidinium salt is the tetramethylguanidinium salt. These examples of salts are not limiting as other salts may also be suitable for use the present invention. One presently preferred salt is the choline salt.

The present invention is also directed to methods of preparation of aqueous compositions comprising salts of (S)-(+)-abscisic acid. In one embodiment, the invention is directed to a method of preparation of the rubidium salt of abscisic acid comprising reacting (S)-(+)-abscisic acid with a chemically equivalent amount of rubidium hydroxide, rubidium bicarbonate or rubidium carbonate in aqueous solution. In another embodiment, the invention is directed to a method of preparation of the cesium salt comprising reacting (S)-(+)-abscisic acid with cesium hydroxide, cesium bicarbonate or cesium carbonate in aqueous solution. In another embodiment, the invention is directed to a method of preparation of the tetramethylammonium salt comprising reacting (S)-(+)-abscisic acid with a chemically equivalent amount of tetramethylammonium hydroxide in aqueous solution. In another embodiment, the invention is directed to a method of preparation of the tetrabutylammonium salt comprising reacting (S)-(+)-abscisic acid with a chemically equivalent amount of tetrabutylammonium hydroxide in aqueous solution. In another embodiment, the invention is directed to a method of preparation of the choline salt comprising reacting (S)-(+)-abscisic acid with choline hydroxide in aqueous solution. In yet another embodiment, the invention is directed to a method of preparation of the tetramethylguanidinium salt comprising reacting (S)-(+)-abscisic acid with one chemical equivalent of tetramethylguanidine in water.

A further embodiment of the invention includes mixtures comprising combinations of salts of S-(+)-abscisic acid prepared with alkali metal cations of high molecular weight or large steric bulk with an effective amount of another salt or a component or multiple components that enhance the long-term chemical stability of the (S)-(+)-abscisic acid and the mixture as a whole. Such components include but are not limited to citric acid or one of its water-soluble salts, sulfur dioxide or a water soluble bisulfate or sulfite salt.

A further embodiment of the invention includes mixtures comprising combinations of salts of S-(+)-abscisic acid prepared with alkali metal cations of high molecular weight or large steric bulk with a substantial amount of a component or multiple components that enhance the biological activity of the (S)-(+)-abscisic acid, including but not limited to iodide salts such as potassium iodide, rubidium iodide, cesium iodide, choline iodide or other quaternary ammonium iodides, guanidines such as guanidinium thiocyanate or tetramethylguanidinium iodide, or a surfactant. Preferred surfactants are gel-forming constituents, such as members of the Brij family.

A presently preferred embodiment of the present invention is an aqueous composition that comprises from about 5 to about 45 weight % of (S) (+)-abscisic acid as the cesium or choline salt and from about 0.1 to about 0.5 weight % potassium sorbate.

Another presently preferred embodiment of the present invention is an aqueous composition that comprises from about 5 to about 45 weight % of (S)-(+)-abscisic acid as the cesium or choline salt; from 0 to about 0.5 weight % potassium sorbate; from about 0.2 to about 1.0 weights % sodium citrate; and from about 0.1 to about 0.5 weight % sodium sulfite.

The disclosed embodiments are exemplary embodiments of the inventive concepts disclosed herein and should not be considered as limiting, unless the claims expressly state otherwise.

DETAILED DESCRIPTION OF THE INVENTION

The present invention relates to aqueous liquid compositions of salts of (S)-(+)-abscisic acid. Abscisic acid is an optically active 15-carbon carboxylic acid. The structural formula of 2-cis-,4-trans-(S)-(+)-abscisic acid is set forth below:

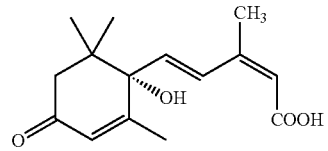

The liquid compositions of the present invention utilize the (S)-(+)-enantiomer and the 2-cis-4-trans-stereochemistry of the carbon chain rather than a racemic mixture of enantiomers and any of the other possible combinations of stereochemistry of the carbon chain. Unless expressly stated otherwise, in all instances when the application refers to abscisic acid or (S)-(+)-abscisic acid, it refers specifically to 2-cis-,4-trans-(S)-(+)-abscisic acid.

In one aspect, the present invention relates to an aqueous composition for the treatment of plants comprising an effective amount of at least one salt of (S)-(+)-abscisic acid prepared with alkali metal cations of high molecular weight or large steric bulk, wherein the concentration of the salt is at least 0.5% by weight of said salt.

As used herein, all numerical values relating to amounts, weight percentages and the like, are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The phrase "effective amount" of a salt means a sufficient amount of the salt to provide the desired biological or chemical effect without at the same time causing additional toxic effects. The amount of salt or other formulation component that is "effective" will vary from composition to composition, depending on the particular agricultural use, the particular salt or salts, and the like. Thus, it is not always possible to specify an exact "effective amount."However, an appropriate "effective amount" in any individual case may be determined by one of ordinary skill in the art using routine experimentation.

Liquid compositions of the present invention can be prepared as either ready-to-use dilutions or dilutable concentrates. According to the present invention, a solution containing from 0.5% to as much as 50% by weight of abscisic acid can be obtained. The dilutable concentrates can be diluted into water directly to a final application concentration or to any intermediate dilution, without risk of precipitation of the active ingredient. The aqueous formulations according to the present invention are inexpensive to manufacture, safe to handle and use, and the (S)-(+)-abscisic acid active ingredient is stable under storage and shipping conditions. With the compositions of the present invention there is no risk of fire as there might be with liquid formulations containing a flammable or combustible organic solvent. There is no risk of contributing to the formation of atmospheric pollution or smog as there is with formulations containing a volatile organic solvent. The aqueous formulations of the present invention are less toxic to humans or animals than similar formulations containing an organic solvent. A person having ordinary skill in the art would be able to determine how to prepare the final aqueous solution concentration for direct application to plants, or how to prepare any intermediate dilutions for use in chemigation equipment or injection diluters or similar equipment, without undue experimentation, without any chance of causing precipitation of the active ingredient and without long and laborious stirring to bring the active ingredient into solution.

The aqueous solution formulations of the present invention may also optionally include an effective amount of an additional ingredient or several additional ingredients in order to enhance the long-term chemical stability of the (S)-(+)-abscisic acid or the formulation as a whole. Such enhancing ingredients include but are not limited to citric acid or one of its water-soluble salts, sulfur dioxide or a water soluble bisulfite or sulfite salt. The use of water as the solvent allows for a combined liquid formulation comprising any or several of these inorganic components that may comprise a level of the enhancing ingredient equal to the concentration of the (S)-(+)-abscisic acid salt or higher, if desired.

The aqueous solution formulations of the present invention may also optionally include a substantial amount of an additional ingredient or several additional ingredients in order to enhance the biological activity of the (S)-(+)-abscisic acid. Such enhancing ingredients include but are not limited to an iodide salt such as potassium iodide, rubidium iodide, cesium iodide, choline iodide, or a tetraalkylammonium iodide, a guanidine salt such as guanidinium thiocyanate or tetramethylguanidinium iodide, or a surfactant. The use of water as the solvent allows for a combined liquid formulation comprising any or several of these inorganic components or urea that may comprise a level of the enhancing ingredient equal to the concentration of the (S)-(+)-abscisic acid salt or even up to 10 times the amount of (S)-(+)-abscisic acid by weight or more. Again, this provides an advantage over the use of an organic solvent, in which these inorganic components or organic salts may have little if any solubility.

Additionally, the aqueous solution formulations of the present invention may optionally include a substantial amount of a surfactant, in an amount equal by weight to the content of (S)-(+)-abscisic acid salt or even several times greater. Examples of surfactants that may be included in the compositions of the present invention include, but are not limited to products of the Brij family of polyoxyethylene fatty alcohol ethers (available from Uniquema, Castle Del.), products of the Tween family of polyoxyethylene sorbitan esters (available from Uniquema, Castle Del.), products of the Silwet family of organosilicones (available from Union Carbide, Lisle Ill.), products of the Triton family of alkylphenol ethoxylates (available from Dow Chemical Company, Midland Mich.), products of the Tomadol family of ethoxylated linear alcohols (available from Tomah3 Products, Inc., Milton Wis.), products of the Myrj family of polyoxyethylene fatty acid esters (available from Uniquema Castle Del.), products of the Trylox family of ethoxylated sorbitol and ethoxylated sorbitol esters (available from Cognis Corporation, Cincinnati Ohio), or any of the specific commercial products Latron B-1956 (available from Rohm & Haas, Philadelphia Pa.), Capsil (available from Aquatrols, Paulsboro N.J.), Agral 90 (available from Norac Concepts, Inc., Orleans ON, Canada), Kinetic (available from Setre, Memphis Term.), or Regulaid (available from KALO, Overland Park Kans.). The presently preferred surfactants are those of the Brij or Tween families. The most preferred surfactants for inclusion in compositions of the present invention are Brij 98, Brij 78, Tween 20 and Tween 40. The concentration of surfactant in the compositions of the invention may range from about 0.02% up to about 40% by weight. The preferred range of concentrations for the surfactant in the compositions of the invention is from about 0.1% to 30% by weight. The most preferred range of concentrations for the surfactant in the compositions of the invention is from about 0.25% to about 25% by weight. The surfactant may be included in the compositions of the present invention either together with any one or more of the inorganic salt or urea activity enhancing ingredients or in the absence of any of them.

The end user can apply compositions of the present invention to plants for various purposes, such as improving stress tolerance, reducing their water utilization, slowing their growth rate, adjusting flowering phase, for seed treatment, preventing preharvest fruit and flower drop and improving the quality and color of fruits. The possible uses may also include, for example, distribution and sale of various concentrated solutions of (S)-(+)-abscisic acid. Utilizing such high concentrations for shipping and handling allows the use of smaller volumes of water, thus simplifying shipping and handling procedures and decreasing costs. The end user could then dilute the product to a 1% concentration (or other percentage depending on the end user's needs) and fill the supply reservoir of mixing equipment for spray or drench application to ornamental bedding plants ready for shipment. Alternatively, another end user could prepare a diluted solution for injection into the drip irrigation system for a vineyard at the appropriate time to enhance the color or phenolic content of a wine or table grape crop.

Representative suitable salts of the invention include, but are not limited to, rubidium or cesium salts, organic quaternary ammonium salts, guanidinium salts or mixtures comprising any number of these. In one embodiment, the organic quaternary ammonium salt is the tetramethylammonium salt. In another embodiment, the organic quaternary ammonium salt is the tetrabutylammonium salt. In another embodiment, the organic quaternary ammonium salt is the choline salt. In yet another embodiment, the guanidinium salt is the tetramethylguanidinium salt. These examples of salts are not limiting as other salts may also be suitable for use the present invention. One presently preferred salt is the choline salt.

Organic quaternary ammonium compounds that may be employed in the salts useful in the compositions of the present invention are those comprising quaternary ammonium cations of the form $R_1R_2R_3R_4N^+$, wherein $R_1$, $R_2$, $R_3$ and $R_4$ are independently lower alkyl, alkenyl or alkynyl of 1 to 6 carbons, arranged in a straight or branched chain and comprising or joined together to form 0 or 1 ring structures and bearing 0, 1 or 2 halogens or hydroxyl groups and wherein one or more R group may bear a phenyl substituent.

In one embodiment, the present invention is directed to a method of preparation of the rubidium salt of abscisic acid comprising reacting (S)-(+)-abscisic acid with a chemically equivalent amount of rubidium hydroxide, rubidium bicarbonate or rubidium carbonate in aqueous solution. In another embodiment, the invention is directed to a method of preparation of the cesium salt comprising reacting (S)-(+)-abscisic acid with cesium hydroxide, cesium bicarbonate or cesium carbonate in aqueous solution. In another embodiment, the invention is directed to a method of preparation of the tetramethylammonium salt comprising reacting (S)-(+)-abscisic acid with a chemically equivalent amount of tetramethylammonium hydroxide in aqueous solution. In another embodiment, the invention is directed to a method of preparation of the tetrabutylammonium salt comprising reacting (S)-(+)-abscisic acid with a chemically equivalent amount of tetrabutylammonium hydroxide in aqueous solution. In another embodiment, the invention is directed to a method of preparation of the choline salt comprising reacting (S)-(+)-abscisic acid with choline hydroxide in aqueous solution. In yet another embodiment, the invention is directed to a method of preparation of the tetramethylguanidinium salt comprising reacting (S)-(+)-abscisic acid with one chemical equivalent of tetramethylguanidine in water.

In a preferred embodiment, at least about 0.25% by weight of Tween-20, a detergent polysorbate, is added to the reaction mixture and resulting formulation when preparing the (S)-(+)-abscisic acid salts.

In another preferred embodiment, the aqueous solution comprises an antimicrobial agent to prevent microbial growth during long-term storage. The presently most preferred antimicrobial agent is potassium sorbate. When the aqueous solution of an (S)-(+)-abscisic acid salt of the present invention is intended for long term storage or for distribution and commercial sale to the user, it is advantageous to incorporate the antimicrobial agent at a concentration of from about 0.01% to about 1.0% by weight.

In another preferred embodiment, the aqueous solution comprises an agent to prevent undesirable development of coloration or appearance of precipitate during long-term storage. The presently most preferred agents for this purpose are sodium or potassium citrate and sodium or potassium sulfite or bisulfite.

In the preferred embodiments, the pH of the concentrated compositions of the invention and any aqueous solutions at final use dilution prepared from the concentrates are both approximately neutral (near pH 7).

Preferred compositions of the present invention comprise from 0.5 to 50 weight % of (S)-(+)-abscisic acid in the form of a salt, from 0.01 to 1.0 weight % of an antimicrobial agent, optionally from about 0.01 to about 5 weight % of a stability enhancing agent, optionally from 0.25 to 35 weight % of a surfactant, optionally from about 1 to about 50 weight % of another activity enhancing component, with the balance being water.

The following examples are intended to illustrate the present invention and to teach one of ordinary skill in the art how to make and use the invention. They are not intended to limit the invention or its protection in any way.

EXAMPLES

Example 1

Preparation of an Aqueous Solution Composition Comprising the Rubidium Salt of (S)-(+)-Abscisic Acid Tween 20 (25 mg), trisodium citrate dihydrate (125 mg) and sodium metabisulfite (62.5 mg) were dissolved in 10 mL of deionized water. (S)-(+)-Abscisic acid (2.64 g of 95% purity) was added, and the mixture was stirred until a smooth suspension was obtained. The solution was titrated with a 50% aqueous solution of rubidium hydroxide to a final pH of 6.8, monitoring with a pH meter, which produced a clear, colorless solution. The solution was then diluted with deionized water to a total weight of 25 g and stored in a brown bottle.

Thus a composition was prepared comprising 10.0% (S)-(+)-abscisic acid by weight as the rubidium salt and further comprising sodium citrate and sodium bisulfite as stability enhancing additives.

Example 2

Preparation of an Aqueous Solution Composition Comprising the Cesium Salt of (S)-(+)-Abscisic Acid Tween 20 (25 mg), trisodium citrate dihydrate (164 mg) and sodium metabisulfite (62.5 mg) were dissolved in 10 mL of deionized water. (S)-(+)-Abscisic acid (2.64 g of 95% purity) was added, and the mixture was stirred until a smooth suspension was obtained. A 50% aqueous solution of cesium hydroxide was added dropwise with good stirring until all of the abscisic acid was brought into solution. The final pH was 6.96. The solution was made up with deionized water to 25.0 g total weight and stored in a brown bottle.

Thus a composition was prepared comprising 10.0% abscisic acid by weight as the cesium salt and further comprising sodium citrate and sodium bisulfite as stability enhancing additives.

Example 3

Preparation of an Aqueous Solution Composition Comprising the Tetramethylammonium Salt of (S)-(+)-Abscisic Acid (S)-(+)-Abscisic acid (2.64 g of 95% purity) was suspended in 10 mL of deionized water in which was dissolved 25 mg of Tween 20, 125 mg of trisodium citrate dihydrate and 62.5 mg of sodium metabisulfite. The mixture was titrated to neutrality (pH 7.0) with a 1.0 molar aqueous solution of tetramethylammonium hydroxide, which resulted in a clear colorless solution. The solution was made up with deionized water to a total weight of 25.0 g and stored in a brown bottle.

Thus a composition was prepared comprising 10.0% abscisic acid by weight as the tetramethylammonium salt and further comprising sodium citrate and sodium bisulfite as stability enhancing additives.

Example 4

Preparation of an Aqueous Solution Composition Comprising the Tetrabutylammonium Salt of (S)-(+)-Abscisic Acid (S)-(+)-Abscisic acid (2.64 g of 95% purity) was suspended in 15 mL of deionized water in which was dissolved 25 mg of Tween 20, 142 mg of trisodium citrate dihydrate and 62.5 mg of sodium metabisulfite. A 40% aqueous solution of tetrabutylammonium hydroxide (approximately 6.5 mL) was added, and the mixture was stirred mechanically until all the abscisic acid was dissolved. The final pH was approximately 8.0. The solution was made up with deionized water to a final total weight of 31.25 g and stored in a brown bottle.

Thus a composition was prepared comprising 8.0% abscisic acid by weight as the tetrabutylammonium salt and further comprising sodium citrate and sodium bisulfite as stability enhancing additives.

Example 5

Preparation of an Aqueous Solution Composition Comprising the Choline Salt of (S)-(+)-abscisic Acid Tween 20 (25 mg), trisodium citrate dihydrate (125 mg) and sodium metabisulfite (62.5 mg) were dissolved in 10 mL of deionized water. (S)-(+)-Abscisic acid (2.64 g of 95% purity) was added, and the mixture was stirred until a smooth suspension was obtained. The mixture was titrated to a pH of 6.9, monitoring with a pH meter, which produced a clear, colorless solution. The solution was then diluted with deionized water to a total weight of 25 g and stored in a brown bottle.

Thus a composition was prepared comprising 10.0% (S)-(+)-abscisic acid by weight as the choline salt and further comprising sodium citrate and sodium bisulfite as stability enhancing additives.

Example 6

Preparation of an Aqueous Solution Composition Comprising the Tetramethylguanidinium Salt of (S)-(+)-Abscisic Acid Tween 20 (25 mg), trisodium citrate dihydrate (164 mg) and sodium metabisulfite (62.5 mg) were dissolved in 10 mL of deionized water. (S)-(+)-Abscisic acid (2.64 g of 95% purity) was added, and the mixture was stirred until a smooth suspension was obtained. Tetramethylguanidine (approximately 1.15 g) was added dropwise with good stirring, monitoring the final drops of the addition with the aid of a pH meter. The final pH, at the point when all the abscisic acid was dissolved, was 6.9. The solution was made up with deionized water to a final total weight of 25.0 g and stored in a brown bottle.

Thus a composition was prepared comprising 10.0% abscisic acid by weight as the tetramethylguanidinium salt and further comprising sodium citrate and sodium bisulfite as stability enhancing additives.

Example 7

Preparation of an Aqueous Solution Composition Comprising the Ammonium Salt of (S)-(+)-Abscisic Acid and Comprising Potassium Iodide as Performance-Enhancing Additive Tween 20 (25 mg), trisodium citrate dihydrate (164 mg) and sodium metabisulfite (62.5 mg) were dissolved in 10 mL of deionized water. (S)-(+)-Abscisic acid (2.64 g of 95% purity) was added, and the mixture was stirred until a smooth suspension was obtained. Commercial concentrated ammonia solution was added dropwise until nearly all the solid abscisic acid had dissolved. Potassium iodide (1.66 g, 1.0 molar equivalent) was added and the mixture was stirred to dissolve it. The pH of the solution was adjusted to 6.5 by addition of a small amount of dilute aqueous ammonia and made up to a total weight of 25.0 g with deionized water.

Thus a composition was prepared comprising 10.0% abscisic acid by weight as the ammonium salt, comprising one equivalent of potassium iodide, and further comprising sodium citrate and sodium bisulfite as stability enhancing additives.

Example 8

Preparation of an Aqueous Solution Composition Comprising the Ammonium Salt of (S)-(+)-Abscisic Acid and Further Comprising Ammonium Iodide as Performance-Enhancing Additive Tween 20 (25 mg), trisodium citrate dihydrate (164 mg) and sodium metabisulfite (62.5 mg) were dissolved in 10 mL of deionized water. Commercial concentrated hydriodic acid (1.28 g, 10 mmoles) was added. (S)-(+)-Abscisic acid (2.64 g of 95% purity, 10 mmoles) was added, and the mixture was stirred until a smooth suspension was obtained. The mixture was titrated to a pH of 7.45 with concentrated aqueous ammonia, producing a clear solution. The solution was made up to a total weight of 25.0 g by addition of deionized water and stored in a brown bottle.

Thus a composition was prepared comprising 10.0% abscisic acid by weight as the ammonium salt, comprising one equivalent of ammonium iodide, and further comprising sodium citrate and sodium bisulfite as stability enhancing additives.

Example 9

Preparation of an Aqueous Solution Composition of the Ammonium Salt Comprising (S)-(+)-Abscisic Acid and Further Comprising Choline Iodide as Performance-Enhancing Additive Tween 20 (25 mg), trisodium citrate dihydrate (164 mg) and sodium metabisulfite (62.5 mg) were dissolved in 8 mL of deionized water. (S)-(+)-Abscisic acid (2.64 g of 95% purity) was added, and the mixture was stirred until a smooth suspension was obtained. Commercial concentrated ammonia solution was added dropwise until nearly all the solid abscisic acid had dissolved. Choline iodide (2.31 g, 1.0 molar equivalent) was added and the mixture was stirred to dissolve it. The pH of the solution was adjusted to 6.8 by addition of a small amount of dilute aqueous ammonia and made up to a total weight of 25 g with deionized water.

Thus a composition was prepared comprising 10.0% abscisic acid by weight as the ammonium salt, comprising one equivalent of choline iodide, and further comprising sodium citrate and sodium bisulfite as stability enhancing additives.

Example 10

Preparation of an Aqueous Solution Composition Comprising the Ammonium Salt of (S)-(+)-Abscisic Acid and Further Comprising Guanidinium Thiocyanate as Performance-Enhancing Additive Tween 20 (25 mg), trisodium citrate dihydrate (142 mg) and sodium metabisulfite (62.5 mg) were dissolved in 10 mL of deionized water. (S)-(+)-Abscisic acid (2.64 g of 95% purity, 10 mmoles) was added, and the mixture was stirred until a smooth suspension was obtained. Commercial concentrated ammonia solution was added dropwise until nearly all the solid abscisic acid had dissolved, and the remainder of the solid was brought into solution by titrating up to pH 6.5 using a 1+9 dilution of concentrated ammonia solution. Guanidinium thiocyanate (1.18 g, 10 mmoles) was added and the solution was stirred to dissolve it. The mixture was transferred to a tared brown bottle and brought up to a total weight of 25 g with deionized water.

Thus a composition was prepared comprising 10.0% abscisic acid by weight as the ammonium salt, comprising one equivalent of guanidinium thiocyanate as performance-enhancing additive, and further comprising sodium citrate and sodium bisulfate as stability enhancing additives.

Comparative Example 11

Preparation of an Aqueous Solution Composition Comprising the Ammonium Salt of (S)-(+)-Abscisic Acid and Further Comprising Potassium Sorbate, Trisodium Citrate and Sodium Sulfite Water (1609 g) was used to make a solution containing 2.0 g Tween 20, 5.0 g potassium sorbate, 5.0 g sodium sulfite and 10 g trisodium citrate. Adding 110 g of (S)-(+)-abscisic acid (95% purity) followed by 20.7 g of concentrated aqueous ammonia allowed most of the abscisic acid to dissolve. After adding a further 101 g of (S)-(+)-abscisic acid and 21.6 g of concentrated ammonia, again most of the abscisic acid was dissolved. Cautious addition of 6.8 g more ammonia solution was required to bring all solid into solution. Water was added to make a total batch weight of 2000 g, and the solution was passed through a 500-mesh screen. The final pH was 6.62.

Thus an aqueous solution composition comprising 10% (S)-(+)-abscisic acid by weight as the ammonium salt and further comprising 0.25% by weight potassium sorbate, 0.25% sodium sulfite and 0.5% by weight trisodium citrate as stability enhancing additives was prepared.

Comparative Example 12

Preparation of an Aqueous Solution Composition Comprising the Potassium Salt of (S)-(+)-Abscisic Acid and Further Comprising Potassium Sorbate, Sodium Metabisulfite and Trisodium Citrate A solution of 25 mg Tween 20, 125 mg trisodium citrate dihydrate and 62.5 mg sodium metabisulfite in 10 mL of deionized water was stirred with 2.64 g of (S)-(+)-abscisic acid of 95% purity until all the powder was in suspension. The mixture was titrated with 3 M KOH to pH 6.87, which dissolved all of the solid. The solution was then diluted with an appropriate amount of deionized water to make it up to 25 g total weight and stored in a brown bottle.

Thus a composition was prepared comprising 10.0% (S)-(+)-abscisic acid by weight as the potassium salt and further comprising sodium citrate and sodium bisulfite as stability enhancing additives.

Comparative Example 13

Preparation of an Aqueous Solution Composition Comprising the Trimethylamine Salt of (S)-(+)-Abscisic Acid Further Comprising Potassium Sorbate (S)-(+)-Abscisic acid (2.64 g of 95% purity) was suspended in 15 mL of deionized water containing 50 mg of Tween 20. An aqueous solution of trimethylamine (1.5 mL of 6.6M concentration) was added, which caused most of the abscisic acid to dissolve. The remainder of the neutralization was then carried out by careful dropwise addition of the aqueous trimethylamine, to give a clear solution of pH 6.8. Preservative (63 mg of potassium sorbate) was added, and it quickly dissolved. The solution was made up with deionized water to 25 mL final volume to give a 10% by weight aqueous composition of (S)-(+)-abscisic acid as a trimethylamine salt.

Comparative Example 14

Preparation of an Aqueous Solution Composition Comprising the Tributylamine Salt of (S)-(+)-Abscisic Acid Tween 20 (25 mg), trisodium citrate dihydrate (164 mg) and sodium metabisulfite (62.5 mg) were dissolved in 10 mL of deionized water. (S)-(+)-Abscisic acid (2.64 g of 95% purity) was added, and the mixture was stirred for about 20 minutes until a smooth suspension was obtained. Adding most of the calculated amount of the tributylamine produced a gum that dissolved only slowly and only with the addition of more water. After extended stirring a homogenous solution was obtained which was titrated to a pH of 6.5 with the remaining stoichiometric amount of tributylamine. The mixture was transferred to a tared brown bottle and made up to a total weight of 50 g, producing a solution comprising 5% by weight (S)-(+)-abscisic acid as the tributylamine salt and further comprising sodium citrate and sodium bisulfite as stability enhancing additives.

Preparation of plant specimens for use in the treatment studies of the EXAMPLES that follow was carried out as follows. Tomato (variety: Rutgers) seeds were sown in an 18-cell flat filled with Promix PGX (available from Premier Horticulture Inc., Quakertown Pa.) and grown for 3 weeks to allow for germination and initial growth. Plants were then transplanted into pots (18 cm in diameter and 18 cm in height), filled with Promix BX (available from Premier Horticulture Inc., Quakertown Pa.), and grown for one or two more weeks before treatment, depending on temperature and available light. Plants received daily irrigation and weekly fertilizer (1 g/L all purpose fertilizer 20-20-20, available from The Scotts Company, Marysville, Ohio).

All treatment solutions were made up with distilled water. The (S)-(+)-abscisic acid (95% active ingredient) is available from Lomon BioTechnology Co., Ltd. (Shichuan, China). The prior art aqueous solution composition of the ammonium salt of (S)-(+)-abscisic acid as prepared in Example 11 above was used as a positive treatment control for most of the studies.

All experiments were conducted using a randomized complete block experimental design. Solutions of (S)-(+)-abscisic acid and blank treatments (plain water) were applied by spray to the aerial parts of the tomato plants at the rate of 24 mL per 6 plants. Plants were then placed in a transparent chamber with humidity controlled within the range of 40 to 60% relative humidity. Leaf transpiration rates were measured at 1, 2, 3, 4 and 7 days after treatment. Measurements were conducted using a LI-1600 Steady State Porometer (LI-Cor, Lincoln, Nebr.). Each day the transpiration rate of the plants of each treatment group was normalized to a percentage of the transpiration rate of untreated plants (plants sprayed with water only) in order to control for day-to-day variability in plant status caused by changes of environmental conditions such as light intensity and temperature. Data for each plant was also averaged over a 3-day period to balance the short term and long term effect of (S)-(+)-abscisic acid on tomato leaf transpiration as well as to reduce experimental variability. It is important to note that no phytotoxicity was observed on any of the plants treated with the compositions of the present invention.

The relationship between relative transpiration rate and the base-10 logarithm of concentration of the (S)-(+)-abscisic acid salt was linear for each salt tested. The regression equation of each (S)-(+)-abscisic acid salt as well as abscisic acid concentrations for 50% inhibition of transpiration were calculated. The relative potency of two ABA salts is the reciprocal of the ratio of (S)-(+)-abscisic acid concentration required for 50% transpiration inhibition for each composition.

Example 15

TABLE 1

Effect of (S)-(+)-abscisic acid ammonium salt of Example 11 vs. (S)-(+)-abscisic acid rubidium salt of Example 1 and its combination with Brij 98 on tomato transpiration inhibition

| Treatment | Transpiration rate (% of control) Days after treatment | | | | | |
|---|---|---|---|---|---|---|
| | 1 | 2 | 3 | 4 | 7 | 7-Day Average |
| Control (water only) | 100.0 | 100.0 | 100.0 | 100.0 | 100.0 | 100.0 |
| 250 ppm Example 11 (1 mg) | 62.1 | 72.7 | 80.4 | 90.9 | 98.2 | 80.9 |
| 250 ppm Example 1 (1 mg) | 55.8 | 68.0 | 76.5 | 88.2 | 91.0 | 75.9 |
| 250 ppm Example 1 + 0.05% Brij 98 | 32.6 | 53.0 | 62.9 | 83.2 | 86.9 | 63.7 |

TABLE 2

Relative potency of (S)-(+)-abscisic acid ammonium salt of Example 11 vs. (S)-(+)-abscisic acid rubidium salt of Example 1 formulations in tomato leaf transpiration inhibition

| (S)-(+)-abscisic acid dose (mg) | Log[(S)-(+)-abscisic acid] | Transpiration rate (% of control) Average of 3 days after treatment | |
|---|---|---|---|
| | | Ammonium salt of Example 11 | Rubidium salt of Example 1 |
| 0.3 | −0.52 | 82 | 77 |
| 1 | 0.00 | 72 | 67 |
| 3 | 0.48 | 60 | 54 |
| 10 | 1.00 | 50 | 39 |
| Equation | | y = 71 − 21x | y = 65 − 25x |
| $R^2$ | | 1.00 | 0.99 |
| ABA dose to achieve 50% inhibition of transpiration (mg) | | 9.71 | 4.05 |

The relative potency of the rubidium salt composition of Example 1 of the present invention compared to that of the ammonium salt composition of Comparative Example 11 is thus 2.4 times, a very substantial enhancement of the biological activity.

In this experiment, the fresh weights of the aerial parts of the tomato plants were also measured at the end of the experiment, 7 days after treatments were applied, in order to assess the relative growth suppressing activity of the compositions. The results are shown in Table 3.

TABLE 3

Effect of (S)-(+)-abscisic acid ammonium salt of Example 11 vs. (S)-(+)-abscisic acid rubidium salt of Example 1 and its in combination with Brij 98 on tomato shoot fresh weight

| Treatments | Fresh weight (g) 7 days after treatment |
|---|---|
| Control (water only) | 18.8 |
| 75 ppm ammonium salt of Example 11 (0.3 mg) | 18.7 |
| 250 ppm ammonium salt of Example 11 (1 mg) | 18.2 |
| 750 ppm ammonium salt of Example 11 (3 mg) | 17.6 |
| 2500 ppm ammonium salt of Example 11 (10 mg) | 16.6 |
| 75 ppm rubidium salt of Example 1 (0.3 mg) | 18.6 |
| 250 ppm rubidium salt of Example 1 (1 mg) | 18.1 |
| 750 ppm rubidium salt of Example 1 (3 mg) | 17.2 |
| 2500 ppm rubidium salt of Example 1 (10 mg) | 16.4 |
| 250 ppm rubidium salt of Example 1 + 0.05% Brij 98 | 17.0 |

The data in Table 3 demonstrate that while the ammonium salt of (S)-(+)-abscisic acid of the composition of Comparative Example 11 is able to retard the growth of tomato plants in a dose-dependent manner, the rubidium salt of (S)-(+)-abscisic acid of the present invention is clearly more effective in retarding the growth in a dose-dependent manner and without producing phytotoxicity. Including a surfactant in the spray solution increases the effect even further, still with no evidence of phytotoxicity at this concentration.

Example 16

TABLE 4

Effect of (S)-(+)-abscisic acid ammonium salt of Example 11 vs.
(S)-(+)-abscisic acid cesium salt of Example 2 and its combination
with Brij 98 on tomato transpiration inhibition

| Treatment | Transpiration rate (% of control) Days after treatment | | | | | 7-Day Average |
|---|---|---|---|---|---|---|
| | 1 | 2 | 3 | 4 | 7 | |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 57.3 | 65.5 | 83.1 | 87.6 | 97.4 | 78.2 |
| 250 ppm Example 2 (1 mg) | 47.1 | 59.0 | 63.9 | 77.8 | 91.1 | 67.8 |
| 250 ppm Example 2 + 0.05% Brij 98 | 27.3 | 45.1 | 54.2 | 63.8 | 85.7 | 55.2 |

TABLE 5

Relative potency of (S)-(+)-abscisic acid ammonium salt of
Example 11 vs. (S)-(+)-abscisic acid cesium salt of Example
2 formulations in tomato leaf transpiration inhibition

| | | Transpiration rate (% of control) Average of 3 days after treatment | |
|---|---|---|---|
| (S)-(+)-abscisic acid dose (mg) | Log[(S)-(+)-abscisic acid] | Ammonium salt of Example 11 | Cesium salt of Example 2 |
| 0.3 | −0.52 | 80 | 72 |
| 1 | 0.00 | 69 | 57 |
| 3 | 0.48 | 58 | 47 |
| 10 | 1.00 | 48 | 37 |
| Equation | | $y = 69 - 21x$ | $y = 59 - 23x$ |
| $R^2$ | | 1.00 | 0.99 |
| ABA dose to achieve 50% inhibition of transpiration (mg) | | 7.73 | 2.41 |

The relative potency of the cesium salt composition of Example 2 of the present invention compared to that of the ammonium salt composition of Comparative Example 11 is thus 3.2 times, a very substantial enhancement of the biological activity.

In this experiment, the fresh weights of the aerial parts of the tomato plants were also measured at the end of the experiment, 7 days after treatments were applied, in order to assess the relative growth suppressing activity of the compositions. The results are shown in Table 6.

TABLE 6

Effect of (S)-(+)-abscisic acid ammonium salt of Example 11
vs. (S)-(+)-abscisic acid cesium salt of Example 2 and its
combination with Brij 98 on tomato shoot fresh weight

| Treatments | Fresh weight (g) 7 days after treatment |
|---|---|
| Control (water only) | 17.0 |
| 75 ppm ammonium salt of Example 11 (0.3 mg) | 16.5 |
| 250 ppm ammonium salt of Example 11 (1 mg) | 16.5 |
| 750 ppm ammonium salt of Example 11 (3 mg) | 16.0 |
| 2500 ppm ammonium salt of Example 11 (10 mg) | 14.7 |
| 75 ppm cesium salt of Example 2 (0.3 mg) | 16.2 |
| 250 ppm cesium salt of Example 2 (1 mg) | 15.3 |
| 750 ppm cesium salt of Example 2 (3 mg) | 14.7 |
| 2500 ppm cesium salt of Example 2 (10 mg) | 11.3 |
| 250 ppm cesium salt of Example 2 + 0.05% Brij 98 | 13.4 |

The data in Table 3 demonstrate that while the (S)-(+)-abscisic acid ammonium salt composition of Comparative Example 11 is able to retard the growth of tomato plants in a dose-dependent manner, the cesium salt of (S)-(+)-abscisic acid of Example 2 the present invention is clearly substantially more effective in retarding the growth in a dose-dependent manner and without producing phytotoxicity. Including a surfactant in the spray solution increases the effect even further, still with no evidence of phytotoxicity at this concentration.

Comparative Example 17

TABLE 7

Effect of S)-(+)-abscisic acid ammonium salt of Example 11 vs.
(S)-(+)-abscisic acid potassium salt of Example 12 on tomato
transpiration inhibition.

| Treatment | Transpiration rate (% of control) Days after treatment | | | | | 7-Day Average |
|---|---|---|---|---|---|---|
| | 1 | 2 | 3 | 4 | 7 | |
| Control (water only) | 100.0 | 100.0 | 100.0 | 100.0 | 100.0 | 100.0 |
| 250 ppm (S)-(+)-abscisic acid ammonium salt of Example 11 (1 mg) | 55.8 | 63.8 | 75.0 | 89.4 | 96.4 | 76.1 |
| 250 ppm (S)-(+)-abscisic acid potassium salt of Example 12 (1 mg) | 55.0 | 64.9 | 76.9 | 90.9 | 97.3 | 77.0 |

TABLE 8

Relative potency of (S)-(+)-abscisic acid ammonium salt of Example
11 and (S)-(+)-abscisic acid potassium salt of Example 12 formulations
in tomato leaf transpiration inhibition

| | | Transpiration rate (% of control) Average of 3 days after treatment | |
|---|---|---|---|
| (S)-(+)-abscisic acid dose (mg) | Log[(S)-(+)-abscisic acid] | Ammonium salt of Example 11 | Potassium salt of Example 12 |
| 0.3 | −0.52 | 77 | 76 |
| 1 | 0.00 | 65 | 66 |
| 3 | 0.48 | 55 | 55 |
| 10 | 1.00 | 44 | 44 |

TABLE 8-continued

Relative potency of (S)-(+)-abscisic acid ammonium salt of Example 11 and (S)-(+)-abscisic acid potassium salt of Example 12 formulations in tomato leaf transpiration inhibition

| | | Transpiration rate (% of control) Average of 3 days after treatment | |
|---|---|---|---|
| (S)-(+)-abscisic acid dose (mg) | Log[(S)-(+)-abscisic acid] | Ammonium salt of Example 11 | Potassium salt of Example 12 |
| Equation | | y = 65 − 22x | y = 65 − 21x |
| $R^2$ | | 1.00 | 1.00 |
| ABA dose to achieve 50% inhibition of transpiration (mg) | | 5.17 | 5.28 |

The relative potency of the prior art potassium salt composition of Comparative Example 12 compared to that of the ammonium salt composition of Comparative Example 11 is thus 0.98 times, a negligible difference in the biological activity.

The data in Tables 7 and 8 clearly show that there is no substantial difference between the biological activity of the ammonium salt formulation of Comparative Example 11 and that of the potassium salt formulation of Comparative Example 12. Thus it is particularly surprising that, as is shown in Examples 15 and 16 above, the rubidium salt formulation of Example 1 and the cesium salt formulation of Example 2 of the present invention have very substantially enhanced biological activity over that of the ammonium salt formulation of Comparative Example 11, since potassium, rubidium and cesium are all alkali metals, adjacent members of the periodic table of elements.

Example 18

TABLE 9

Effect of (S)-(+)-abscisic acid ammonium salt of Comparative Example 11 and (S)-(+)-abscisic acid tetrabutylammonium salt of Example 4 and its combination with Brij 98 on tomato transpiration inhibition

| | Transpiration rate (% of control) Days after treatment | | | | | | |
|---|---|---|---|---|---|---|---|
| Treatment | 1 | 2 | 3 | 4 | 7 | 9 | 9-Day Average |
| Control (water only) | 100.0 | 100.0 | 100.0 | 100.0 | 100.0 | 100.0 | 100.0 |
| 250 ppm (S)-(+)-abscisic acid as the ammonium salt of Example 11 (1 mg) | 66.1 | 82.7 | 84.6 | 89.2 | 100.6 | 100.8 | 87.3 |
| 250 ppm tetrabutylammonium salt of Example 4 (1 mg) | 63.4 | 73.9 | 77.8 | 79.3 | 89.2 | 94.6 | 79.7 |
| 250 ppm tetrabutylammonium salt of Example 4 + 0.05% Brij 98 | 32.6 | 62.0 | 66.0 | 70.2 | 83.3 | 91.7 | 67.6 |

TABLE 10

Relative potency of (S)-(+)-abscisic acid ammonium salt of Comparative Example 11 and (S)-(+)-abscisic acid tetrabutylammonium salt of Example 4 formulation in tomato leaf transpiration inhibition

| | | Transpiration rate (% of control) Average of first 3 days after treatment | |
|---|---|---|---|
| (S)-(+)-abscisic acid dose (mg) | Log[(S)-(+)-abscisic acid] | Ammonium salt of Example 11 | Tetrabutylammonium salt of Example 4 |
| 0.3 | −0.52 | 95 | 84 |
| 1 | 0.00 | 78 | 72 |
| 3 | 0.48 | 67 | 56 |
| 10 | 1.00 | 53 | 38 |
| Equation | | y = 79 − 27x | y = 70 − 31x |
| $R^2$ | | 1.00 | 0.99 |
| ABA dose to achieve 50% inhibition of transpiration (mg) | | 12.21 | 4.35 |

The relative potency of the tetrabutylammonium salt composition of Example 2 of the present invention compared to that of the ammonium salt composition of Comparative Example 11 is thus 2.8 times, a very substantial enhancement of the biological activity.

Example 19

TABLE 11

Effect of (S)-(+)-abscisic acid tributylamine salt of Example 14 vs. the tetrabutylammonium salt of Example 4 on tomato transpiration inhibition

| | Transpiration rate (% of control) Days after treatment | | | | | |
|---|---|---|---|---|---|---|
| Treatment | 1 | 2 | 3 | 4 | 7 | 7-Day Average |
| Control (water only) | 100.0 | 100.0 | 100.0 | 100.0 | 100.0 | 100.0 |
| 250 ppm tributylamine salt of Example 14 (1 mg) | 59.7 | 71.3 | 78.8 | 87.4 | 100.3 | 79.5 |
| 250 ppm tetrabutylammonium salt of Example 4 (1 mg) | 55.1 | 61.0 | 68.3 | 77.6 | 92.4 | 70.9 |

TABLE 12

Relative potency of (S)-(+)-abscisic acid tributylamine salt of Example 14 vs. the tetrabutylammonium salt of Example 4 formulations in tomato leaf transpiration inhibition

| | | Transpiration rate (% of control) Average of 3 days after treatment | |
|---|---|---|---|
| (S)-(+)-abscisic acid dose (mg) | Log[(S)-(+)-abscisic acid] | Tetrabutylammonium salt of Example 4 | Tributylamine salt of Example 14 |
| 0.3 | −0.52 | 80 | 82 |
| 1 | 0.00 | 61 | 70 |
| 3 | 0.48 | 47 | 53 |
| 10 | 1.00 | 29 | 40 |
| Equation | | y = 62 − 33x | y = 68 − 28x |
| $R^2$ | | 1.00 | 0.99 |
| ABA dose to achieve 50% inhibition of transpiration (mg) | | 2.33 | 4.34 |

The relative potency of the tetrabutylammonium salt composition of Example 4 of the present invention compared to that of the tributylamine salt composition of Comparative Example 14 is thus 1.9 times, a substantial difference in the biological activity. This is particularly surprising, since both cations are composed of nitrogen bearing the same type of alkyl group and differ only in the number of butyl groups.

In this experiment, the fresh weights of the aerial parts of the tomato plants were also measured at the end of the experiment, 7 days after treatments were applied, in order to assess the relative growth suppressing activity of the compositions. The results are shown in Table 13.

TABLE 13

Effect of (S)-(+)-abscisic acid tributylamine salt of Example 14 vs. the tetrabutylammonium salt of Example 4 on tomato shoot fresh weight

| Treatments | Fresh weight (g) 7 days after treatment |
| --- | --- |
| Control (water only) | 15.7 |
| 75 ppm tributylamine salt of Example 14 (0.3 mg) | 15.7 |
| 250 ppm tributylamine salt of Example 14 (1 mg) | 15.3 |
| 750 ppm tributylamine salt of Example 14 (3 mg) | 15.0 |
| 2500 ppm tributylamine salt of Example 14 (10 mg) | 13.9 |
| 75 ppm tetrabutylammonium salt of Example 4 (0.3 mg) | 15.3 |
| 250 ppm tetrabutylammonium salt of Example 4 (1 mg) | 14.8 |
| 750 ppm tetrabutylammonium salt of Example 4 (3 mg) | 12.5 |
| 2500 ppm tetrabutylammonium salt of Example 4 (10 mg) | 11.4 |

The data in Table 13 demonstrate that while the tributylamine salt of (S)-(+)-abscisic acid of the composition of Comparative Example 14 is able to retard the growth of tomato plants in a dose-dependent manner, the tetrabutylammonium salt of (S)-(+)-abscisic acid Example 4 of the present invention is clearly substantially more effective in retarding the growth in a dose-dependent manner, without producing phytotoxicity.

Example 20

TABLE 14

Effect of (S)-(+)-abscisic acid trimethylamine salt of Example 13 vs. the tetramethylammonium salt of Example 3 and combination with Brij 98 on tomato transpiration inhibition

| | Transpiration rate (% of control) Days after treatment | | | | | |
| --- | --- | --- | --- | --- | --- | --- |
| Treatment | 1 | 2 | 3 | 4 | 7 | 7-Day Average |
| Control (water only) | 100.0 | 100.0 | 100.0 | 100.0 | 100.0 | 100.0 |
| 250 ppm (S)-(+)-abscisic acid trimethylamine salt of Example 13 (1 mg) | 65.5 | 73.6 | 81.7 | 88.2 | 97.0 | 81.2 |
| 250 ppm tetramethylammonium salt of Example 3 (1 mg) | 59.1 | 63.6 | 71.9 | 78.6 | 95.4 | 73.7 |
| 250 ppm tetramethylammonium salt of Example 3 + 0.05% Brij 98 | 34.7 | 49.5 | 56.8 | 68.9 | 89.9 | 60.0 |

TABLE 15

Relative potency of (S)-(+)-abscisic acid trimethylamine salt of Example 13 vs. the tetramethylammonium salt of Example 3 formulations in tomato leaf transpiration inhibition

| | | Transpiration rate (% of control) Average of 3 days after treatment | |
| --- | --- | --- | --- |
| (S)-(+)-abscisic acid dose (mg) | Log[(S)-(+)-abscisic acid] | Trimethylamine salt of Example 13 | Tetramethylammonium salt of Example 3 |
| 0.3 | −0.52 | 84 | 79 |
| 1 | 0.00 | 74 | 65 |
| 3 | 0.48 | 65 | 52 |
| 10 | 1.00 | 54 | 38 |
| Equation | | y = 74 − 20x | y = 65 − 27x |
| $R^2$ | | 1.00 | 1.00 |
| ABA dose to achieve 50% inhibition of transpiration (mg) | | 16.59 | 3.59 |

The data presented in Tables 14 and 15 show that the relative potency of the tetramethyl-ammonium salt composition of Example 3 of the present invention compared to that of the trimethylamine salt composition of Comparative Example 13 is 4.6 times, a very substantial increase in the biological activity. This is particularly surprising, since both cations are composed of nitrogen bearing the same type of alkyl group and differ only in the number of methyl groups, 3 vs. 4.

Example 21

TABLE 16

Effect of (S)-(+)-abscisic acid ammonium salt of Comparative Example 11 and (S)-(+)-abscisic acid choline salt of Example 5 and its combination with Brij 98 on tomato transpiration inhibition

| | Transpiration rate (% of control) Days after treatment | | | | | |
| --- | --- | --- | --- | --- | --- | --- |
| Treatment | 1 | 2 | 3 | 4 | 7 | 7-Day Average |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 61.1 | 70.3 | 83.4 | 88.4 | 97.3 | 80.1 |
| 250 ppm choline salt of Example 5 (1 mg) | 52.3 | 63.7 | 73.8 | 79.0 | 93.4 | 72.5 |
| 250 ppm choline salt of Example 5 + 0.05% Brij 98 | 38.0 | 52.3 | 63.7 | 68.1 | 87.8 | 62.0 |

TABLE 17

Relative potency of (S)-(+)-abscisic acid ammonium salt of Comparative Example 11 and (S)-(+)-abscisic acid choline salt of Example 5 formulations in tomato leaf transpiration inhibition

| | | Transpiration rate (% of control) Average of 3 days after treatment | |
| --- | --- | --- | --- |
| (S)-(+)-abscisic acid dose (mg) | Log[(S)-(+)-abscisic acid] | Ammonium salt of Example 11 | Choline salt of Example 5 |
| 0.3 | −0.52 | 82 | 78 |
| 1 | 0.00 | 72 | 63 |

TABLE 17-continued

Relative potency of (S)-(+)-abscisic acid ammonium salt of
Comparative Example 11 and (S)-(+)-abscisic acid choline salt
of Example 5 formulations in tomato leaf transpiration inhibition

| | | Transpiration rate (% of control) Average of 3 days after treatment | |
|---|---|---|---|
| (S)-(+)-abscisic acid dose (mg) | Log[(S)-(+)-abscisic acid] | Ammonium salt of Example 11 | Choline salt of Example 5 |
| 3 | 0.48 | 60 | 53 |
| 10 | 1.00 | 51 | 41 |
| Equation | | y = 71 − 21x | y = 65 − 24x |
| $R^2$ | | 1.00 | 1.00 |
| ABA dose to achieve 50% inhibition of transpiration (mg) | | 10.49 | 4.02 |

The relative potency of the choline salt composition of Example 5 of the present invention compared to that of the ammonium salt composition of Comparative Example 11 is thus 2.6 times, a very substantial enhancement of the biological activity.

In this experiment, the fresh weights of the aerial parts of the tomato plants were also measured at the end of the experiment, 7 days after treatments were applied, in order to assess the relative growth suppressing activity of the compositions. The results are shown in Table 18.

TABLE 18

Effect of (S)-(+)-abscisic acid ammonium salt of Comparative Example 11 and (S)-(+)-abscisic acid choline salt of Example 5 and its combination with Brij 98 on tomato shoot fresh weight

| Treatments | Fresh weight (g) 7 days after treatment |
|---|---|
| Control (water only) | 18.4 |
| 75 ppm (S)-(+)-abscisic acid as the ammonium salt of Example 11 (0.3 mg) | 18.4 |
| 250 ppm (S)-(+)-abscisic acid as the ammonium salt of Example 11 (1 mg) | 17.9 |
| 750 ppm (S)-(+)-abscisic acid as the ammonium salt of Example 11 (3 mg) | 17.3 |
| 2500 ppm (S)-(+)-abscisic acid as the ammonium salt of Example 11 (10 mg) | 16.6 |
| 75 ppm choline salt of Example 5 (0.3 mg) | 18.2 |
| 250 ppm choline salt of Example 5 (1 mg) | 17.5 |
| 750 ppm choline salt of Example 5 (3 mg) | 16.8 |
| 2500 ppm choline salt of Example 5 (10 mg) | 16.0 |
| 250 ppm choline salt of Example 5 + 0.05% Brij 98 | 16.5 |

The data in Table 18 demonstrate that while the ammonium salt of (S)-(+)-abscisic acid of the composition of Comparative Example 11 is able to retard the growth of tomato plants in a dose-dependent manner, the choline salt of (S)-(+)-abscisic acid the composition of Example 5 of the present invention is clearly more effective in retarding the growth in a dose-dependent manner, without producing phytotoxicity. Including a surfactant in the spray solution increases the effect even further, still with no evidence of phytotoxicity at this concentration.

Example 22

TABLE 19

Effect of (S)-(+)-abscisic acid ammonium salt of Comparative Example 11 and (S)-(+)-abscisic acid tetramethylguanidinium salt of Example 6 and its combination with Brij 98 on tomato transpiration inhibition

| | Transpiration rate (% of control) Days after treatment | | | | | |
|---|---|---|---|---|---|---|
| Treatment | 1 | 2 | 3 | 4 | 7 | 7-Day Average |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 59.8 | 69.6 | 81.1 | 89.6 | 97.1 | 79.4 |
| 250 ppm tetramethylguanidinium salt of Example 6 (1 mg) | 51.0 | 61.3 | 71.2 | 79.9 | 90.3 | 70.8 |
| 250 ppm tetramethylguanidinium salt of Example 6 + 0.05% Brij 98 | 30.7 | 37.1 | 55.8 | 67.6 | 95.6 | 57.3 |

TABLE 20

Relative potency of (S)-(+)-abscisic acid as the ammonium salt of Example 11 and V0367-080 salt formulation in tomato leaf transpiration inhibition

| | | Transpiration rate (% of control) Average of 3 days after treatment | |
|---|---|---|---|
| (S)-(+)-abscisic acid dose (mg) | Log[(S)-(+)-abscisic acid] | Ammonium salt of Example 11 | Tetramethylguanidinium salt of Example 6 |
| 0.3 | −0.52 | 80 | 71 |
| 1 | 0.00 | 70 | 61 |
| 3 | 0.48 | 59 | 42 |
| 10 | 1.00 | 48 | 31 |
| Equation | | y = 69 − 21x | y = 58 − 28x |
| $R^2$ | | 1.00 | 0.98 |
| ABA dose to achieve 50% inhibition of transpiration (mg) | | 8.16 | 1.93 |

The relative potency of the tetramethylguanidinium salt composition of Example 5 of the present invention compared to that of the ammonium salt composition of Comparative Example 11 is thus 4.2 times, a very substantial enhancement of the biological activity.

Example 23

TABLE 21

Enhanced effect of (S)-(+)-abscisic acid as the ammonium salt of the composition of Example 7 and further enhancement by its combination with Brij 98 on tomato transpiration inhibition

| | Transpiration rate (% of control) Days after treatment | | | | | |
|---|---|---|---|---|---|---|
| Treatment | 1 | 2 | 3 | 4 | 7 | 7-Day Average |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 65.2 | 68.1 | 85.1 | 87.1 | 94.0 | 79.9 |

TABLE 21-continued

Enhanced effect of (S)-(+)-abscisic acid as the ammonium salt of the composition of Example 7 and further enhancement by its combination with Brij 98 on tomato transpiration inhibition

| Treatment | Transpiration rate (% of control) Days after treatment | | | | | |
|---|---|---|---|---|---|---|
| | 1 | 2 | 3 | 4 | 7 | 7-Day Average |
| 250 ppm (S)-(+)-abscisic acid composition of Example 7 (1 mg) | 53.0 | 58.0 | 65.3 | 70.8 | 78.8 | 65.2 |
| 250 ppm composition of Example 7 + 0.05% Brij 98 | 30.8 | 44.2 | 48.2 | 63.6 | 78.3 | 53.0 |

TABLE 22

Relative potency of (S)-(+)-abscisic acid as the ammonium salt of Example 11 and the composition of Example 7 of the present invention in tomato leaf transpiration inhibition

| (S)-(+)-abscisic acid dose (mg) | Log[(S)-(+)-abscisic acid] | Transpiration rate (% of control) Average of 3 days after treatment | |
|---|---|---|---|
| | | Ammonium salt of Example 11 | Composition of Example 7 |
| 0.3 | −0.52 | 90 | 86 |
| 1 | 0.00 | 72 | 59 |
| 3 | 0.48 | 55 | 44 |
| 10 | 1.00 | 48 | 38 |
| Equation | | y = 73 − 28x | y = 64 − 32x |
| $R^2$ | | 0.97 | 0.92 |
| ABA dose to achieve 50% inhibition of transpiration (mg) | | 6.51 | 2.84 |

The relative potency of the composition of Example 7 of the present invention compared to that of the ammonium salt composition of Comparative Example 11 is thus 2.3 times, a very substantial enhancement of the biological activity.

In this experiment, the fresh weights of the aerial parts of the tomato plants were also measured at the end of the experiment, 7 days after treatments were applied, in order to assess the relative growth suppressing activity of the compositions. The results are shown in Table 23.

TABLE 23

Effect of (S)-(+)-abscisic acid as the ammonium salt of Example 11 and the composition of Example 7 of the present invention and its combination with Brij 98 on tomato shoot fresh weight

| Treatments | Fresh weight (g) 7 days after treatment |
|---|---|
| Control (water only) | 6.2 |
| 75 ppm (S)-(+)-abscisic acid as the ammonium salt of Example 11 (0.3 mg) | 6.2 |
| 250 ppm (S)-(+)-abscisic acid as the ammonium salt of Example 11 (1 mg) | 5.7 |
| 750 ppm (S)-(+)-abscisic acid as the ammonium salt of Example 11 (3 mg) | 5.8 |
| 2500 ppm (S)-(+)-abscisic acid as the ammonium salt of Example 11 (10 mg) | 4.1 |
| 75 ppm (S)-(+)-abscisic acid as the composition of Example 7 (0.3 mg) | 4.6 |
| 250 ppm (S)-(+)-abscisic acid as the composition of Example 7 (1 mg) | 5.2 |
| 750 ppm (S)-(+)-abscisic acid as the composition of Example 7 (3 mg) | 4.9 |
| 2500 ppm (S)-(+)-abscisic acid as the composition of Example 7 (10 mg) | 3.3 |
| 250 ppm (S)-(+)-abscisic acid as the composition of Example 7 + 0.05% Brij 98 | 4.2 |

The data in Table 23 demonstrate that while the ammonium salt of (S)-(+)-abscisic acid of the composition of Comparative Example 11 is able to retard the growth of tomato plants in a dose-dependent manner, the composition of (S)-(+)-abscisic acid of Example 7 of the present invention is clearly more effective in retarding the growth in a dose-dependent manner, without producing phytotoxicity. Including a surfactant in the spray solution increases the effect even further, still with no evidence of phytotoxicity at this concentration.

Example 24

TABLE 24

Enhanced effect of (S)-(+)-abscisic acid as the ammonium salt of the composition of Example 8 and further enhancement by its combination with Brij 98 on tomato transpiration inhibition.

| Treatment | Transpiration rate (% of control) Days after treatment | | | | | |
|---|---|---|---|---|---|---|
| | 1 | 2 | 3 | 4 | 7 | 7-Day Average |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 62.1 | 72.0 | 82.5 | 88.4 | 97.4 | 80.5 |
| 250 ppm (S)-(+)-abscisic acid as the composition of Example 8 (1 mg) | 59.3 | 69.2 | 77.1 | 84.8 | 97.0 | 77.5 |
| 250 ppm (S)-(+)-abscisic acid as the composition of Example 8 + 0.05% Brij 98 | 43.0 | 55.6 | 65.1 | 73.2 | 89.5 | 65.3 |

TABLE 25

Relative potency of (S)-(+)-abscisic acid as the ammonium salt of Comparative Example 11 and as the composition of Example 8 of the present invention in tomato leaf transpiration inhibition

| (S)-(+)-abscisic acid dose (mg) | Log[(S)-(+)-abscisic acid] | Transpiration rate (% of control) Average of 3 days after treatment | |
|---|---|---|---|
| | | (S)-(+)-abscisic acid as the ammonium salt of Example 11 | (S)-(+)-abscisic acid as the composition of Example 8 |
| 0.3 | −0.52 | 81 | 78 |
| 1 | 0.00 | 72 | 69 |
| 3 | 0.48 | 60 | 57 |

TABLE 25-continued

Relative potency of (S)-(+)-abscisic acid as the ammonium salt
of Comparative Example 11 and as the composition of Example 8 of
the present invention in tomato leaf transpiration inhibition

| (S)-(+)-abscisic acid dose (mg) | Log[(S)-(+)-abscisic acid] | Transpiration rate (% of control) Average of 3 days after treatment | |
|---|---|---|---|
| | | (S)-(+)-abscisic acid as the ammonium salt of Example 11 | (S)-(+)-abscisic acid as the composition of Example 8 |
| 10 | 1.00 | 52 | 47 |
| Equation | | y = 71 − 20x | y = 68 − 21x |
| $R^2$ | | 0.99 | 1.00 |
| ABA dose to achieve 50% inhibition of transpiration (mg) | | 11.71 | 7.12 |

The relative potency of the composition of Example 8 of the present invention compared to that of the ammonium salt composition of Comparative Example 11 is thus 1.6 times, a substantial enhancement of the biological activity.

Example 25

TABLE 26

Enhanced effect of (S)-(+)-abscisic acid as the ammonium
salt of the composition of Example 9 and further enhancement
by its combination with Brij 98 on tomato transpiration inhibition.

| Treatment | Transpiration rate (% of control) Days after treatment | | | | | 7-Day Average |
|---|---|---|---|---|---|---|
| | 1 | 2 | 3 | 4 | 7 | |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 68.7 | 78.7 | 83.3 | 87.5 | 94.6 | 82.6 |
| 250 ppm (S)-(+)-abscisic acid as the composition of Example 9 (1 mg) | 62.5 | 69.1 | 77.3 | 83.1 | 93.0 | 77.0 |
| 250 ppm (S)-(+)-abscisic acid as the composition of Example 9 + 0.05% Brij 98 | 48.1 | 50.8 | 58.6 | 70.5 | 82.3 | 62.1 |

TABLE 27

Relative potency of (S)-(+)-abscisic acid as the ammonium salt
of Comparative Example 11 and as the composition of Example 9 of
the present invention in tomato leaf transpiration inhibition.

| (S)-(+)-abscisic acid dose (mg) | Log[(S)-(+)-abscisic acid] | Transpiration rate (% of control) Average of 3 days after treatment | |
|---|---|---|---|
| | | (S)-(+)-abscisic acid as the ammonium salt of Example 11 | (S)-(+)-abscisic acid as the composition of Example 9 |
| 0.3 | −0.52 | 88 | 83 |
| 1 | 0.00 | 77 | 70 |
| 3 | 0.48 | 62 | 57 |
| 10 | 1.00 | 55 | 49 |
| Equation | | y = 76 − 23x | y = 70 − 23x |
| $R^2$ | | 0.98 | 0.99 |
| ABA dose to achieve 50% inhibition of transpiration (mg) | | 14.06 | 7.71 |

The data in Tables 27 and 28 show that the relative potency of the composition of Example 9 of the present invention compared to that of the ammonium salt composition of Comparative Example 11 is 1.8 times, a substantial enhancement of the biological activity.

In this experiment, the fresh weights of the aerial parts of the tomato plants and their heights were also measured at the end of the experiment, 7 days after treatments were applied, in order to assess the relative growth suppressing activity of the compositions. The results are shown in Table 28.

TABLE 28

Effect of (S)-(+)-abscisic acid as the ammonium salt
of Comparative Example 11 and as the composition of Example
9 of the present invention and its combination with Brij
98 on tomato shoot fresh weight and plant height.

| Treatments | 7 days after treatment | |
|---|---|---|
| | Fresh weight (g) | Plant height (cm) |
| Control (water only) | 23.2 | 19.8 |
| 75 ppm (S)-(+)-abscisic acid as the ammonium salt of Example 11 (0.3 mg) | 23.0 | 19.9 |
| 250 ppm (S)-(+)-abscisic acid as the ammonium salt of Example 11 (1 mg) | 22.0 | 19.8 |
| 750 ppm (S)-(+)-abscisic acid as the ammonium salt of Example 11 (3 mg) | 20.9 | 18.6 |
| 2500 ppm (S)-(+)-abscisic acid as the ammonium salt of Example 11 (10 mg) | 20.3 | 18.6 |
| 75 ppm (S)-(+)-abscisic acid as the composition of Example 9 (0.3 mg) | 20.8 | 19.3 |
| 250 ppm (S)-(+)-abscisic acid as the composition of Example 9 (1 mg) | 20.4 | 19.4 |
| 750 ppm (S)-(+)-abscisic acid as the composition of Example 9 (3 mg) | 17.6 | 18.5 |
| 2500 ppm (S)-(+)-abscisic acid as the composition of Example 9 (10 mg) | 14.2 | 16.3 |
| 250 ppm (S)-(+)-abscisic acid as the composition of Example 9 + 0.05% Brij 98 | 17.6 | 18.5 |

The data in Table 28 demonstrate that while the ammonium salt of (S)-(+)-abscisic acid of the composition of Comparative Example 11 is able to retard the growth of tomato plants, as measured by both their heights and weights, in a dose-dependent manner, the composition of (S)-(+)-abscisic acid of Example 9 of the present invention is clearly more effective in retarding the growth in a dose-dependent manner, without producing phytotoxicity. Including a surfactant in the spray solution increases the effect even further, still with no evidence of phytotoxicity at this concentration.

Example 26

TABLE 29

Enhanced effect of (S)-(+)-abscisic acid as the ammonium
salt of the composition of Example 10 and further enhancement
by its combination with Brij 98 on tomato transpiration inhibition.

| Treatment | Transpiration rate (% of control) Days after treatment | | | | | 7-Day Average |
|---|---|---|---|---|---|---|
| | 1 | 2 | 3 | 4 | 7 | |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 61.2 | 70.6 | 81.3 | 88.5 | 96.9 | 79.7 |

TABLE 29-continued

Enhanced effect of (S)-(+)-abscisic acid as the ammonium salt of the composition of Example 10 and further enhancement by its combination with Brij 98 on tomato transpiration inhibition.

| Treatment | Transpiration rate (% of control) Days after treatment | | | | | |
|---|---|---|---|---|---|---|
|  | 1 | 2 | 3 | 4 | 7 | 7-Day Average |
| 250 ppm (S)-(+)-abscisic acid as the composition of Example 10 (1 mg) | 53.6 | 59.2 | 76.6 | 82.6 | 92.5 | 72.9 |
| 250 ppm (S)-(+)-abscisic acid as the composition of Example 10 + 0.05% Brij 98 | 37.9 | 40.6 | 57.2 | 66.1 | 81.0 | 56.6 |

TABLE 30

Relative potency of (S)-(+)-abscisic acid as the ammonium salt of Comparative Example 11 and as the composition of Example 10 of the present invention in tomato leaf transpiration inhibition.

| (S)-(+)-abscisic acid dose (mg) | Log[(S)-(+)-abscisic acid] | Transpiration rate (% of control) Average of 3 days after treatment | |
|---|---|---|---|
|  |  | (S)-(+)-abscisic acid as the ammonium salt of Example 11 | (S)-(+)-abscisic acid as the composition of Example 10 |
| 1 | 0.00 | 71 | 63 |
| 3 | 0.48 | 57 | 52 |
| 10 | 1.00 | 49 | 43 |
| Equation |  | y = 70 − 22x | y = 63 − 20x |
| $R^2$ |  | 0.97 | 0.99 |
| ABA dose to achieve 50% inhibition of transpiration (mg) |  | 8.02 | 4.24 |

The relative potency of the composition of Example 10 of the present invention compared to that of the ammonium salt composition of Comparative Example 11 is thus 1.9 times, a substantial enhancement of the biological activity.

In this experiment, the fresh weights of the aerial parts of the tomato plants were also measured at the end of the experiment, 7 days after treatments were applied, in order to assess the relative growth suppressing activity of the compositions. The results are shown in Table 31.

TABLE 31

Effect of (S)-(+)-abscisic acid as the ammonium salt of Comparative Example 11 and as the composition of Example 10 of the present invention and its combination with Brij 98 on tomato shoot fresh weight.

| Treatments | Fresh weight (g) 7 days after treatment |
|---|---|
| Control (water only) | 4.9 |
| 250 ppm (S)-(+)-abscisic acid as the ammonium salt of Example 11 (1 mg) | 4.3 |
| 750 ppm (S)-(+)-abscisic acid as the ammonium salt of Example 11 (3 mg) | 4.0 |
| 2500 ppm (S)-(+)-abscisic acid as the ammonium salt of Example 11 (10 mg) | 1.7 |
| 250 ppm (S)-(+)-abscisic acid as the composition of Example 10 (1 mg) | 4.1 |
| 750 ppm (S)-(+)-abscisic acid as the composition of Example 10 (3 mg) | 3.3 |
| 2500 ppm (S)-(+)-abscisic acid as the composition of Example 10 (10 mg) | 2.1 |
| 250 ppm (S)-(+)-abscisic acid as the composition of Example 10 + 0.05% Brij 98 | 3.1 |

The data in Table 31 demonstrate that while the ammonium salt of (S)-(+)-abscisic acid of the composition of Comparative Example 11 is able to retard the growth of tomato plants, as measured by both their heights and weights, in a dose-dependent manner, the composition of (S)-(+)-abscisic acid of Example 10 of the present invention is clearly more effective in retarding the growth in a dose-dependent manner, without producing phytotoxicity. Including a surfactant in the spray solution increases the effect even further, still with no evidence of phytotoxicity at this concentration.

Example 27

In this experiment choline iodide was applied at increasing dose rates together with the ammonium salt composition of Example 11, held at a fixed dose rate, in order to study the dose response of this performance-enhancing additive of the present invention. The results are shown in Table 32.

TABLE 32

Enhancement by choline iodide (ChI) and its combination with Brij 98 of the effect of (S)-(+)-abscisic acid on tomato leaf transpiration inhibition

| Treatment | Transpiration rate (% of control) Days after treatment | | | | | |
|---|---|---|---|---|---|---|
|  | 1 | 2 | 3 | 4 | 7 | 7-Day Average |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 63.2 | 80.0 | 88.3 | 90.9 | 98.1 | 84.1 |
| 250 ppm (S)-(+)-abscisic acid as the ammonium salt of Example 11 + 231 ppm ChI | 58.0 | 68.2 | 73.0 | 79.3 | 95.9 | 74.9 |
| 250 ppm (S)-(+)-abscisic acid as the ammonium salt of Example 11 + 462 ppm ChI | 38.5 | 46.8 | 52.5 | 72.3 | 92.6 | 60.5 |

TABLE 32-continued

Enhancement by choline iodide (ChI) and its combination with Brij 98 of the effect of (S)-(+)-abscisic acid on tomato leaf transpiration inhibition

| Treatment | Transpiration rate (% of control) Days after treatment | | | | | |
|---|---|---|---|---|---|---|
| | 1 | 2 | 3 | 4 | 7 | 7-Day Average |
| 250 ppm (S)-(+)-abscisic acid as the ammonium salt of Example 11 + 1155 ppm ChI | 25.9 | 36.8 | 45.3 | 69.9 | 89.9 | 53.6 |
| 250 ppm (S)-(+)-abscisic acid as the ammonium salt of Example 11 + 231 ppm ChI + 0.05% Brij 98 | 24.6 | 40.8 | 65.8 | 70.5 | 91.3 | 58.6 |
| 250 ppm (S)-(+)-abscisic acid as the ammonium salt of Example 11 + 462 ppm ChI + 0.05% Brij 98 | 24.6 | 37.2 | 58.1 | 65.8 | 87.0 | 54.5 |
| 250 ppm (S)-(+)-abscisic acid as the ammonium salt of Example 11 + 1155 ppm ChI + 0.05% Brij 98 | 23.8 | 34.6 | 54.5 | 62.2 | 79.6 | 50.9 |
| 462 ppm ChI | 96.4 | 104.2 | 104.5 | 98.9 | 98.9 | 100.6 |
| 462 ppm ChI + 0.05% Brij 98 | 97.7 | 103.4 | 111.3 | 103.1 | 100.3 | 103.2 |

Note that neither choline iodide alone nor choline iodide plus Brij 98 have any substantial effect on the rate of transpiration in the absence of (S)-(+)-abscisic acid (last two lines of Table 32).

Example 28

In this experiment the tetramethylguanidinium salt composition of Example 6, held at a fixed dose rate, was applied together with increasing dose rates of choline iodide in order to study the dose response of this performance-enhancing additive of the present invention. The same set of doses was also applied with the addition of Brij 98 as well. The results are shown in Table 33.

The data in Table 33 demonstrate that the enhanced performance of the (S)-(+)-abscisic acid salts of the present invention can be further enhanced by incorporating one of the performance-enhancing additives of the present invention and yet further by the additional incorporation of a surfactant. No phytotoxicity was observed in any treatment.

In this experiment, the fresh weights of the aerial parts of the tomato plants were also measured at the end of the experiment, 7 days after treatments were applied, in order to assess

TABLE 33

Effect of (S)-(+)-abscisic acid as the tetramethylguanidinium salt of Example 6 plus choline iodide (ChI) and their combination with Brij 98 on tomato shoot fresh weight.

| Treatment | Transpiration rate (% of control) Days after treatment | | | | | |
|---|---|---|---|---|---|---|
| | 1 | 2 | 3 | 4 | 7 | 7-Day Average |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 65.8 | 76.3 | 87.6 | 95.3 | 100.6 | 85.1 |
| 250 ppm (S)-(+)-abscisic acid as the tetramethylguanidinium salt of Example 6 | 51.9 | 64.3 | 75.6 | 89.9 | 99.1 | 76.2 |
| 250 ppm (S)-(+)-abscisic acid as the tetramethylguanidinium salt of Example 6 + 231 ppm ChI | 47.2 | 57.5 | 71.0 | 85.9 | 98.1 | 72.0 |
| 250 ppm (S)-(+)-abscisic acid as the tetramethylguanidinium salt of Example 6 + 462 ppm ChI | 41.4 | 52.2 | 66.3 | 79.9 | 96.5 | 67.2 |
| 250 ppm (S)-(+)-abscisic acid as the tetramethylguanidinium salt of Example 6 + 1155 ppm ChI | 37.7 | 46.7 | 62.0 | 73.8 | 94.5 | 62.9 |
| 250 ppm (S)-(+)-abscisic acid as the tetramethylguanidinium salt of Example 6 + 0.05% Brij 98 | 35.7 | 46.6 | 61.1 | 78.3 | 93.7 | 63.1 |
| 250 ppm (S)-(+)-abscisic acid as the tetramethylguanidinium salt of Example 6 + 231 ppm ChI + 0.05% Brij 98 | 32.4 | 43.6 | 54.8 | 71.8 | 91.1 | 58.7 |
| 250 ppm (S)-(+)-abscisic acid as the tetramethylguanidinium salt of Example 6 + 462 ppm ChI + 0.05% Brij 98 | 29.6 | 41.4 | 51.6 | 67.6 | 88.7 | 55.8 |
| 250 ppm (S)-(+)-abscisic acid as the tetramethylguanidinium salt of Example 6 + 1155 ppm ChI + 0.05% Brij 98 | 28.7 | 37.9 | 48.1 | 63.0 | 86.7 | 52.9 | the relative growth suppressing activity of the compositions. The results are shown in Table 34.

TABLE 34

Effect of (S)-(+)-abscisic acid as the tetramethylguanidinium salt of Example 6, choline iodide (ChI) and their combination with Brij 98 on tomato shoot fresh weight.

| Treatments | Fresh weight (g) 7 days after treatment |
|---|---|
| Control (water only) | 15.3 |
| 250 ppm (S)-(+)-abscisic acid as the ammonium salt of Example 11 (1 mg) | 13.9 |
| 250 ppm (S)-(+)-abscisic acid as the tetramethylguanidinium salt of Example 6 | 13.4 |
| 250 ppm (S)-(+)-abscisic acid as the tetramethylguanidinium salt of Example 6 + 231 ppm ChI | 13.5 |
| 250 ppm (S)-(+)-abscisic acid as the tetramethylguanidinium salt of Example 6 + 462 ppm ChI | 13.4 |
| 250 ppm (S)-(+)-abscisic acid as the tetramethylguanidinium salt of Example 6 + 1155 ppm ChI | 12.8 |
| 250 ppm (S)-(+)-abscisic acid as the tetramethylguanidinium salt of Example 6 + 0.05% Brij 98 | 13.3 |
| 250 ppm (S)-(+)-abscisic acid as the tetramethylguanidinium salt of Example 6 + 231 ppm ChI + 0.05% Brij 98 | 13.1 |
| 250 ppm (S)-(+)-abscisic acid as the tetramethylguanidinium salt of Example 6 + 462 ppm ChI + 0.05% Brij 98 | 12.9 |
| 250 ppm (S)-(+)-abscisic acid as the tetramethylguanidinium salt of Example 6 + 1155 ppm ChI + 0.05% Brij 98 | 12.5 |

The data in Table 34 demonstrate a dose-dependent enhancement of the growth suppressing effect of (S)-(+)-abscisic acid, in the form of the composition of Example 6 of the present invention, by the incorporation of choline iodide, one of the performance-enhancing additives of the present invention. Thus two aspects of the invention can be employed at the same time, to further increase the effectiveness. Employing a surfactant in addition increases the effect yet further.

Example 29

In this experiment the tetramethylguanidinium salt composition of Example 6, held at a fixed dose rate, was applied together with increasing dose rates of cesium iodide in order to study the dose response of this performance-enhancing additive of the present invention. The high dose of cesium iodide was also applied in combination with a high dose rate of choline iodide, a second performance-enhancing additive of the present invention. The results are shown in Table 35.

TABLE 35

Effect of (S)-(+)-abscisic acid as the tetramethylguanidinium salt of Example 6 plus cesium iodide (CsI) and their combination with choline iodide (ChI) on tomato transpiration.

| Treatment | Transpiration rate (% of control) Days after treatment | | | | | 7-Day Average |
|---|---|---|---|---|---|---|
| | 1 | 2 | 3 | 4 | 7 | |
| Control (water only) | 100.0 | 100.0 | 100.0 | 100.0 | 100.0 | 100.0 |
| 250 ppm (S)-(+)-abscisic acid as the ammonium salt of Example 11 (1 mg) | 71.9 | 82.2 | 96.7 | 100.2 | 99.9 | 90.2 |
| 250 ppm (S)-(+)-abscisic acid as the tetramethylguanidinium salt of Example 6 | 47.8 | 69.0 | 84.5 | 93.2 | 99.0 | 78.7 |
| 250 ppm (S)-(+)-abscisic acid as the tetramethylguanidinium salt of Example 6 + 260 ppm CsI | 45.3 | 66.8 | 81.3 | 90.1 | 98.5 | 76.4 |
| 250 ppm (S)-(+)-abscisic acid as the tetramethylguanidinium salt of Example 6 + 520 ppm CsI | 43.4 | 65.3 | 80.0 | 87.9 | 93.6 | 74.0 |
| 250 ppm (S)-(+)-abscisic acid as the tetramethylguanidinium salt of Example 6 + 1300 ppm CsI | 41.7 | 63.7 | 79.9 | 86.3 | 92.2 | 72.8 |
| 250 ppm (S)-(+)-abscisic acid as the tetramethylguanidinium salt of Example 6 + 1300 ppm CsI + 1155 ppm ChI | 40.1 | 61.5 | 78.9 | 83.6 | 90.7 | 71.0 |

Also in this experiment, the fresh weights of the aerial parts of the tomato plants and their heights were also measured at the end of the experiment, 7 days after treatments were applied, in order to assess the relative growth suppressing activity of the compositions. The results are shown in Table 36.

TABLE 36

Effect of (S)-(+)-abscisic acid as the tetramethylguanidinium salt of Example 6 plus cesium iodide (CsI) and their combination with choline iodide (ChI) on tomato shoot fresh weight and plant height

| Treatments | 7 days after treatment | |
|---|---|---|
| | Average fresh weight (g) | Average plant height (cm) |
| Control (water only) | 40.2 | 33.5 |
| 250 ppm (S)-(+)-abscisic acid as the ammonium salt of Example 11 (1 mg) | 41.8 | 32.1 |
| 250 ppm (S)-(+)-abscisic acid as the tetramethylguanidinium salt of Example 6 | 30.6 | 30.1 |
| 250 ppm (S)-(+)-abscisic acid as the tetramethylguanidinium salt of Example 6 + 260 ppm CsI | 29.9 | 29.2 |
| 250 ppm (S)-(+)-abscisic acid as the tetramethylguanidinium salt of Example 6 + 520 ppm CsI | 28.4 | 28.7 |
| 250 ppm (S)-(+)-abscisic acid as the tetramethylguanidinium salt of Example 6 + 1300 ppm CsI | 26.5 | 28.1 |
| 250 ppm (S)-(+)-abscisic acid as the tetramethylguanidinium salt of Example 6 + 1300 ppm CsI + 1155 ppm ChI | 24.6 | 27.8 |

The data presented in Tables 35 and 36 clearly show the enhancement of the efficacy of (S)-(+)-abscisic acid by the tetramethylguaninidinium salt composition of Example 6 of the present invention and further the additional enhancement in a dose-dependent manner by incorporation of cesium iodide, one of the performance-enhancing additives of the present invention. Finally, the last entry in Tables 35 and 36 shows the further enhancement achieved by incorporating two of the performance-enhancing additives of the present invention in a single composition with a performance-enhancing salt of the present invention. No phytotoxicity was observed in any of the treatments.

Example 30

In this experiment the prior art ammonium salt composition of Example 11, held at a fixed dose rate, was applied together with increasing dose rates of potassium iodide in order to study the dose response of this performance-enhancing additive of the present invention. The same set of doses was also applied with the addition of Brij 98 as well. The results are shown in Table 37.

TABLE 37

Effect of potassium iodide (KI) and its combination with Brij 98 on (S)-(+)-abscisic acid related tomato leaf transpiration inhibition

| | Transpiration rate (% of control) | | | | |
|---|---|---|---|---|---|
| | Days after treatment | | | | |
| Treatment | 1 | 2 | 3 | 4 | 4 Day Average |
| Control (water only) | 100.0 | 100.0 | 100.0 | 100.0 | 100.0 |
| 250 ppm (S)-(+)-abscisic acid as the ammonium salt of Example 11 (1 mg) | 52.6 | 69.5 | 84.2 | 95.3 | 75.4 |
| 250 ppm (S)-(+)-abscisic acid as the ammonium salt of Example 11 + 166 ppm KI | 45.8 | 56.0 | 80.4 | 99.1 | 70.3 |
| 250 ppm (S)-(+)-abscisic acid as the ammonium salt of Example 11 + 332 ppm KI | 52.9 | 62.8 | 82.9 | 99.5 | 74.5 |
| 250 ppm (S)-(+)-abscisic acid as the ammonium salt of Example 11 + 830 ppm KI | 56.9 | 61.5 | 83.7 | 97.9 | 75.0 |
| 250 ppm (S)-(+)-abscisic acid as the ammonium salt of Example 11 + 166 ppm KI + 0.05% Brij 98 | 30.6 | 50.0 | 69.1 | 94.8 | 61.1 |
| 250 ppm (S)-(+)-abscisic acid as the ammonium salt of Example 11 + 332 ppm KI + 0.05% Brij 98 | 30.3 | 46.8 | 71.4 | 91.9 | 60.1 |
| 250 ppm (S)-(+)-abscisic acid as the ammonium salt of Example 11 + 830 ppm KI + 0.05% Brij 98 | 39.9 | 44.3 | 71.2 | 91.7 | 61.8 |
| 332 ppm KI | 100.2 | 100.5 | 99.6 | 102.6 | 100.7 |
| 332 ppm KI + 0.05% Brij 98 | 97.1 | 98.6 | 94.9 | 100.7 | 97.8 |

The data in Table 37 demonstrate that potassium iodide, a performance enhancing additive of the present invention, does increase the transpiration inhibition effectiveness of abscisic acid; however the relationship of dose to effect is not linear.

Example 31

In this experiment the prior art ammonium salt composition of Example 11, held at a fixed dose rate, was applied together with increasing dose rates of cesium nitrate or lithium iodide in order to study the dose response of these performance-enhancing additives of the present invention. The lowest rate of each of the performance-enhancing additives was also applied with the addition of Brij 98. The results are shown in Table 38.

TABLE 37

Effect of potassium iodide (KI) and its combination with Brij 98 on
(S)-(+)-abscisic acid related tomato leaf transpiration inhibition

| Treatment | Transpiration rate (% of control) Days after treatment | | | | |
|---|---|---|---|---|---|
| | 1 | 2 | 3 | 4 | 7 |
| Control | 100.0 | 100.0 | 100.0 | 100.0 | 100.0 |
| 250 ppm (S)-(+)-abscisic acid as the ammonium salt of Example 11 (1 mg) | 76.5 | 82.9 | 90.0 | 95.1 | 100.5 |
| 250 ppm (S)-(+)-abscisic acid as the ammonium salt of Example 11 + 195 ppm CsNO$_3$ | 69.3 | 75.3 | 83.3 | 88.2 | 95.8 |
| 250 ppm (S)-(+)-abscisic acid as the ammonium salt of Example 11 + 390 ppm CsNO$_3$ | 62.6 | 68.7 | 76.5 | 81.4 | 88.6 |
| 250 ppm (S)-(+)-abscisic acid as the ammonium salt of Example 11 + 975 ppm CsNO$_3$ | 55.9 | 61.5 | 69.8 | 75.9 | 82.2 |
| 250 ppm (S)-(+)-abscisic acid as the ammonium salt of Example 11 + 195 ppm CsNO$_3$ + 0.05% Brij 98 | 34.1 | 48.7 | 65.7 | 86.4 | 88.7 |
| 250 ppm (S)-(+)-abscisic acid as the ammonium salt of Example 11 + 134 ppm LiI | 65.4 | 72.7 | 80.4 | 86.6 | 95.5 |
| 250 ppm (S)-(+)-abscisic acid as the ammonium salt of Example 11 + 268 ppm LiI | 58.3 | 66.0 | 72.1 | 81.0 | 89.1 |
| 250 ppm (S)-(+)-abscisic acid as the ammonium salt of Example 11 + 670 ppm LiI | 50.3 | 57.2 | 65.3 | 75.2 | 84.0 |
| 250 ppm (S)-(+)-abscisic acid as the ammonium salt of Example 11 + 134 ppm LiI + 0.05% Brij 98 | 27.3 | 40.8 | 60.4 | 81.3 | 90.7 |

The data in Table 38 clearly demonstrate that either cesium nitrate or lithium iodide, which are performance enhancing additives of the present invention, does increase the transpiration inhibition effectiveness of abscisic acid quite substantially, in a dose-dependent manner. The effect is increased by inclusion of a surfactant, and enhancement by the salt additives is more persistent than the enhancement produced by the surfactant.

Accordingly, it has surprisingly been found that the (S)-(+)-abscisic acid salt compositions of the present invention are substantially more effective when applied to plants than prior art salt compositions of abscisic acid, while retaining low phytotoxicity.

The invention claimed is:

1. A salt or mixture of salts of (S)-(+)-abscisic acid selected from the group consisting of the rubidium salt, tetramethylammonium salt, tetraethylammonium salt, tetrapropylammonium salt, tetrabutylammonium salt, choline salt, dimethylpiperidinium salt, and chloroethyltrimethylammonium salt.

2. The salt of claim 1, wherein said salt is the rubidium salt.

3. The salt of claim 1, wherein said salt is the tetramethylammonium salt.

4. The salt of claim 1, wherein said salt is the tetraethylammonium salt.

5. The salt of claim 1, wherein said salt is the tetrapropylammonium salt.

6. The salt of claim 1, wherein said salt is the tetrabutylammonium salt.

7. The salt of claim 1, wherein said salt is the choline salt.

8. The salt of claim 1, wherein said salt is the dimethylpiperidinium salt.

9. The salt of claim 1, wherein said salt is the chloroethyltrimethylammonium salt.

10. A guanidinium salt or mixture of guanidinium salts of (S)-(+)-abscisic acid, wherein the guanidine may bear 1 to 5 methyl or ethyl groups.

11. The salt of claim 10, wherein said salt is the tetramethylguanidinium salt.

12. A mixture of salts of (S)-(+)-abscisic acid comprising a guanidinium salt of (S)-(+) abscisic acid and a salt of claim 1; wherein the guanidine may bear 1 to 5 methyl or ethyl groups.

13. An aqueous composition for treatment of plants comprising at least one salt or mixture of salts of (S)-(+)-abscisic acid of claim 1, wherein the concentration of the salt is at least 0.5% by weight of said composition; an antimicrobial agent; a surfactant, optionally one or more performance enhancing additives; and optionally one or more additives to stabilize the color.

14. The composition of claim 13, wherein the concentration of the salt is at least 2% by weight of said composition.

15. The composition of claim 13 that further comprises an antimicrobial agent.

16. The composition of claim 15, wherein said antimicrobial agent is potassium sorbate.

17. The composition of claim 13 that further comprises one or more performance-enhancing additives.

18. The composition of claim 17 wherein said performance-enhancing additives are iodide salts selected from the group consisting of potassium iodide, rubidium iodide; cesium iodide; lithium iodide; sodium iodide; tetramethylguanidinium iodide and quaternary ammonium iodide of the form $R_1R_2R_3R_4N^+I^-$, wherein $R_1$, $R_2$, $R_3$ and $R_4$ are independently lower alkyl, alkenyl or alkynyl of 1 to 6 carbons arranged in a straight or branched chain and comprising or joined together to form 0 or 1 ring structures and bearing 0, 1 or 2 halogens or hydroxyl groups, and wherein one or more R group may bear a phenyl substituent.

19. The composition of claim 17 wherein said performance-enhancing additive is choline iodide.

20. The composition of claim 17 wherein said performance-enhancing additive is a water-soluble cesium salt.

21. The composition of claim 20 wherein said performance-enhancing additive is cesium nitrate, $CsNO_3$.

22. The composition of claim 16 that further comprises one or more additives to stabilize the color.

23. The composition of claim 22 wherein said color-stabilizing additive is a sodium or potassium salt of citric acid or sodium or potassium sulfite, bisulfite or metabisulfite.

24. An aqueous composition that comprises from about 5 to about 45 weight % of (S)-(+)- abscisic acid in the form a salt of claim 1; from 0 to about 1 weight % potassium sorbate; from about 0.2 to about 2.0 weight % sodium citrate; and from about 0.1 to about 2 weight % sodium sulfite.

25. An aqueous composition that comprises from about 5 to about 45 weight % of (S)-(+)- abscisic acid in the form a salt of claim 1; from 0 to about 1 weight % potassium sorbate; from about 0.2 to about 2.0 weight % sodium citrate; and from about 0.1 to about 2 weight % sodium sulfite, comprising also a performance-enhancing salt of claim 18 or claim 20.

* * * * *